United States Patent
Huebner et al.

(10) Patent No.: US 8,523,919 B2
(45) Date of Patent: Sep. 3, 2013

(54) TARGETING GUIDE WITH A RADIOPAQUE MARKER TO FACILITATE POSITIONING A BONE PLATE ON BONE

(75) Inventors: Randall J. Huebner, Portland, OR (US); Joshua P. Federspiel, Portland, OR (US); Carol-Lynn E. Connors, Portland, OR (US); James C. Ritter, Indianapolis, IN (US)

(73) Assignee: Acumed LLC, Hillsboro, OR (US)

( * ) Notice: Subject to any disclaimer, the term of this patent is extended or adjusted under 35 U.S.C. 154(b) by 133 days.

(21) Appl. No.: 13/246,690

(22) Filed: Sep. 27, 2011

(65) Prior Publication Data

US 2012/0078252 A1    Mar. 29, 2012

Related U.S. Application Data

(60) Provisional application No. 61/386,921, filed on Sep. 27, 2010, provisional application No. 61/390,120, filed on Oct. 5, 2010.

(51) Int. Cl.
*A61B 17/88* (2006.01)

(52) U.S. Cl.
USPC ............. 606/280; 606/96; 606/97; 606/281

(58) Field of Classification Search
USPC .................. 606/281, 86 B, 280, 282, 96–97, 606/104
See application file for complete search history.

(56) References Cited

U.S. PATENT DOCUMENTS

| | | | |
|---|---|---|---|
| 6,520,969 B2 | 2/2003 | Lambrecht et al. | |
| 2005/0085818 A1 | 4/2005 | Huebner | |
| 2005/0159747 A1 | 7/2005 | Orbay | |
| 2005/0234472 A1 | 10/2005 | Huebner | |
| 2006/0116679 A1 * | 6/2006 | Lutz et al. | 606/69 |
| 2006/0161168 A1 | 7/2006 | Matthys | |
| 2007/0173843 A1 | 7/2007 | Matityahu | |
| 2008/0015590 A1 | 1/2008 | Sanders et al. | |
| 2008/0086123 A1 | 4/2008 | Gotfried | |
| 2008/0281330 A1 | 11/2008 | Ferrante et al. | |
| 2009/0088767 A1 | 4/2009 | Leyden et al. | |
| 2009/0157086 A1 | 6/2009 | Digeser et al. | |
| 2009/0228047 A1 | 9/2009 | Derouet et al. | |
| 2010/0137873 A1 | 6/2010 | Grady, Jr. et al. | |

FOREIGN PATENT DOCUMENTS

| | | |
|---|---|---|
| EP | 1661525 A3 | 2/2007 |
| EP | 2072016 A1 | 6/2009 |
| WO | 03063682 A2 | 8/2003 |
| WO | 2004008972 A3 | 1/2004 |
| WO | 2005099593 A1 | 10/2005 |
| WO | 2009121144 A1 | 10/2009 |

OTHER PUBLICATIONS

United Kingdom Intellectual Property Office; Patents Act 1977, Combined Search and Examination Report under Sections 17 & 18(3); U.K. Patent Application Serial No. GB1207498.5 (counterpart); report dated May 16, 2012.
Zimmer, "Periarticular Distal Femoral Locking Plate: Surgical Technique", 2005, 97-2347-044-00 Rev. 1 7.5 ML.

* cited by examiner

*Primary Examiner* — Andrew Yang
(74) *Attorney, Agent, or Firm* — Kolisch Hartwell, P.C.

(57) ABSTRACT

Bone fixation system, including methods, apparatus, and kits, and comprising a bone plate and at least one instrument that attaches to the bone plate and provides at least one radiopaque region to facilitate positioning the bone plate on bone visualized by radiographic imaging. The instrument may be a handle assembly and/or a targeting guide.

19 Claims, 5 Drawing Sheets

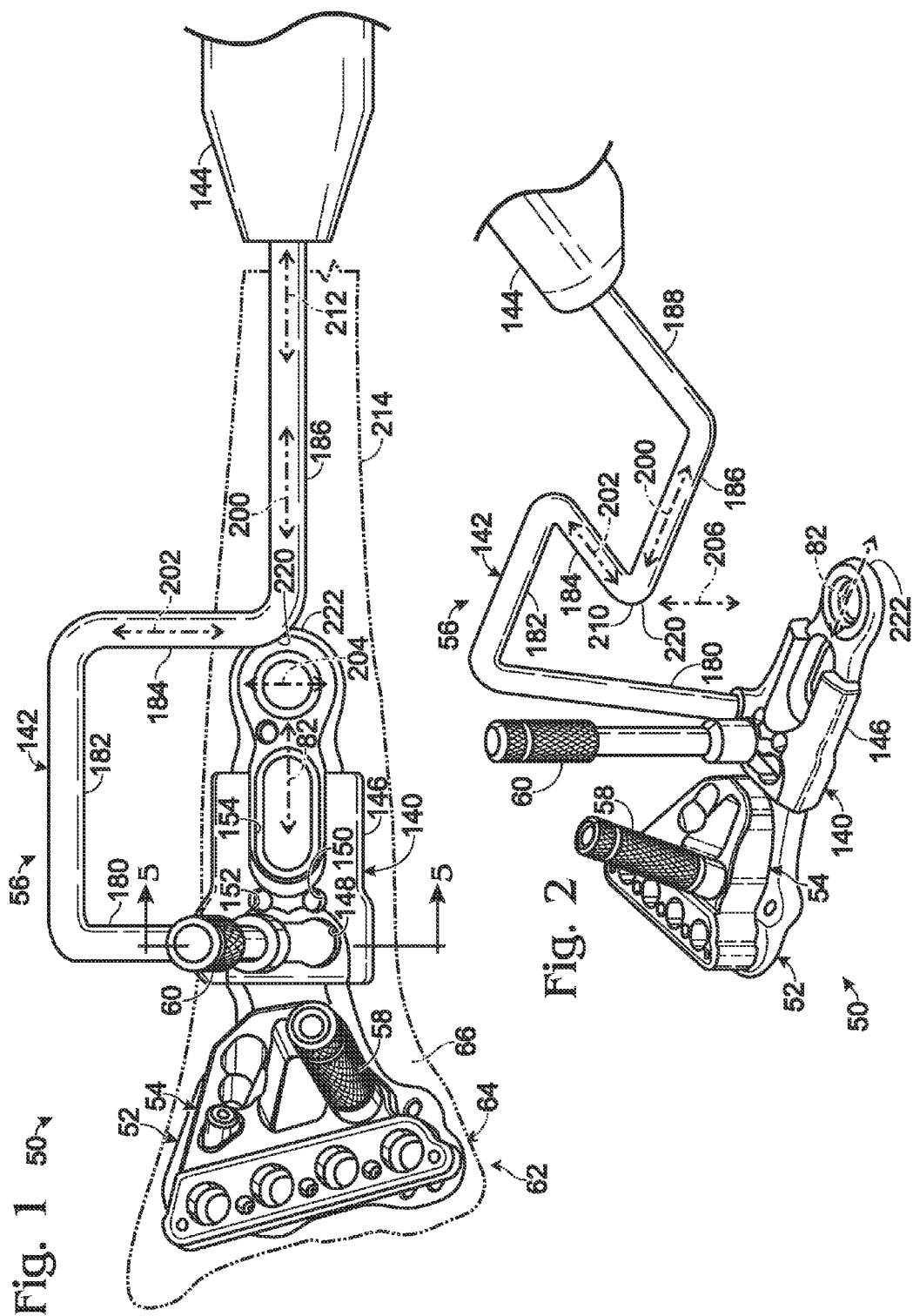

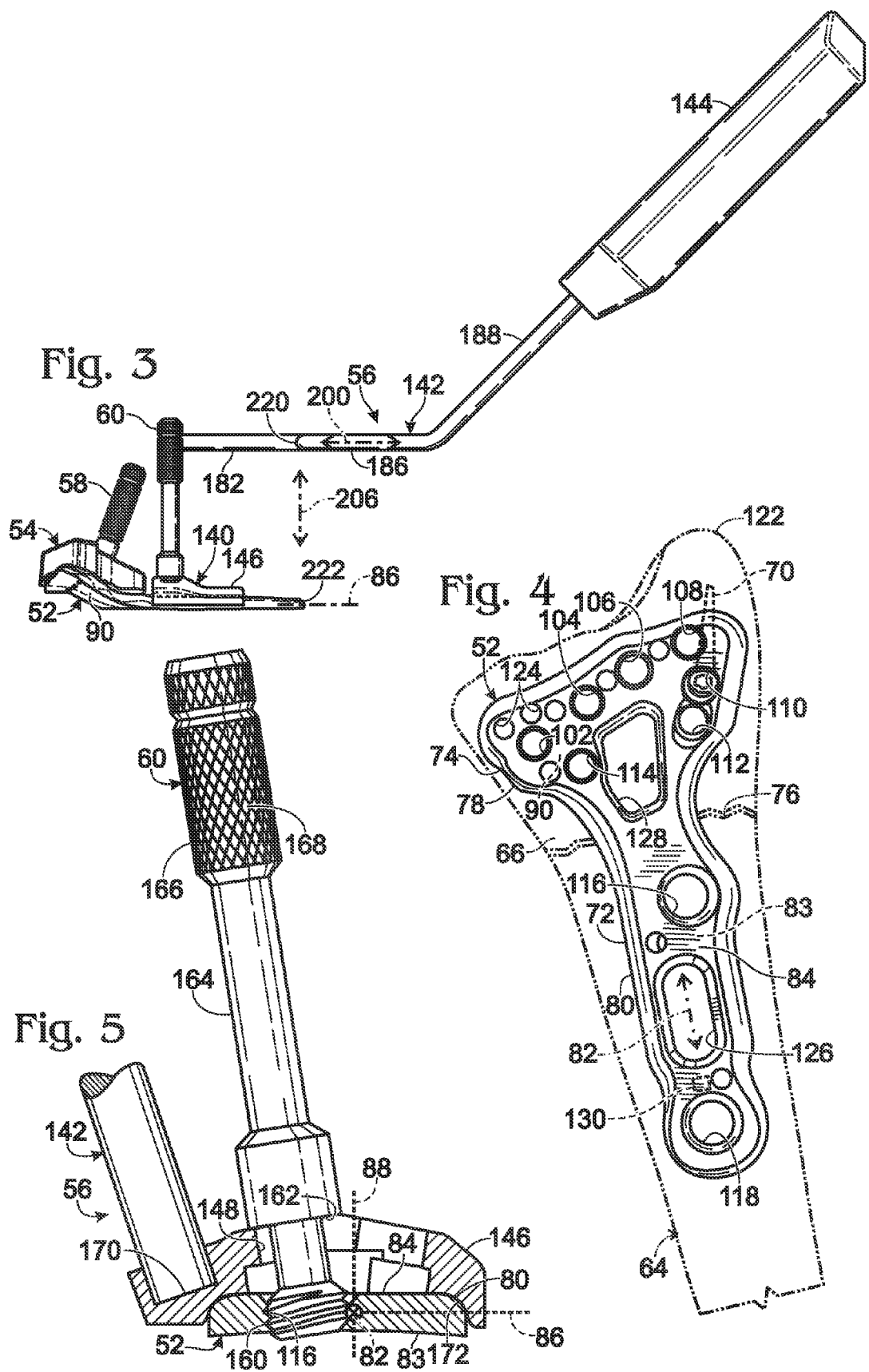

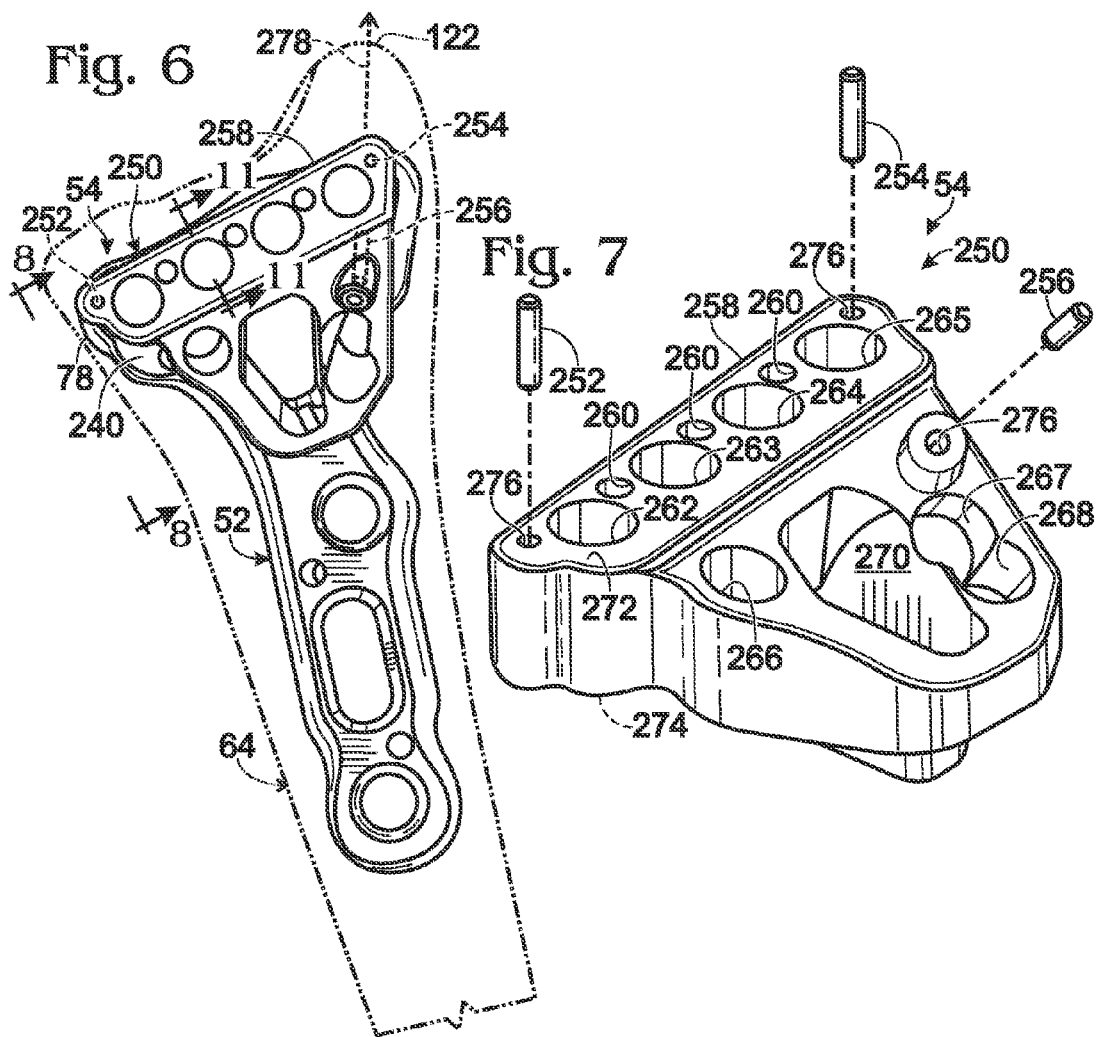
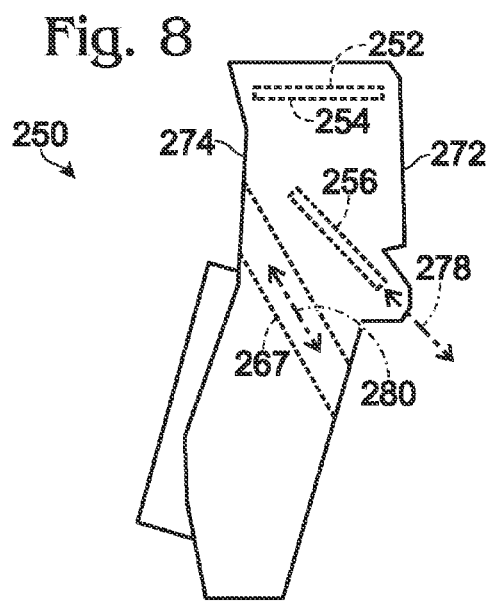
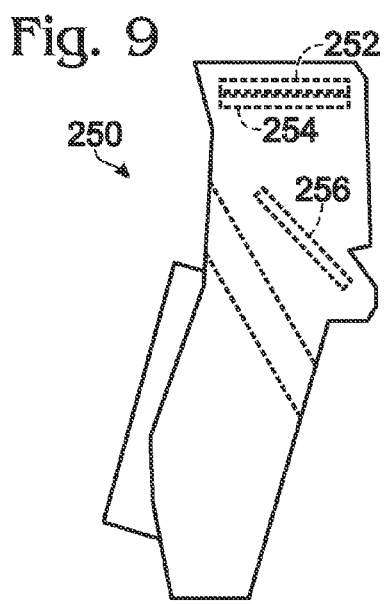

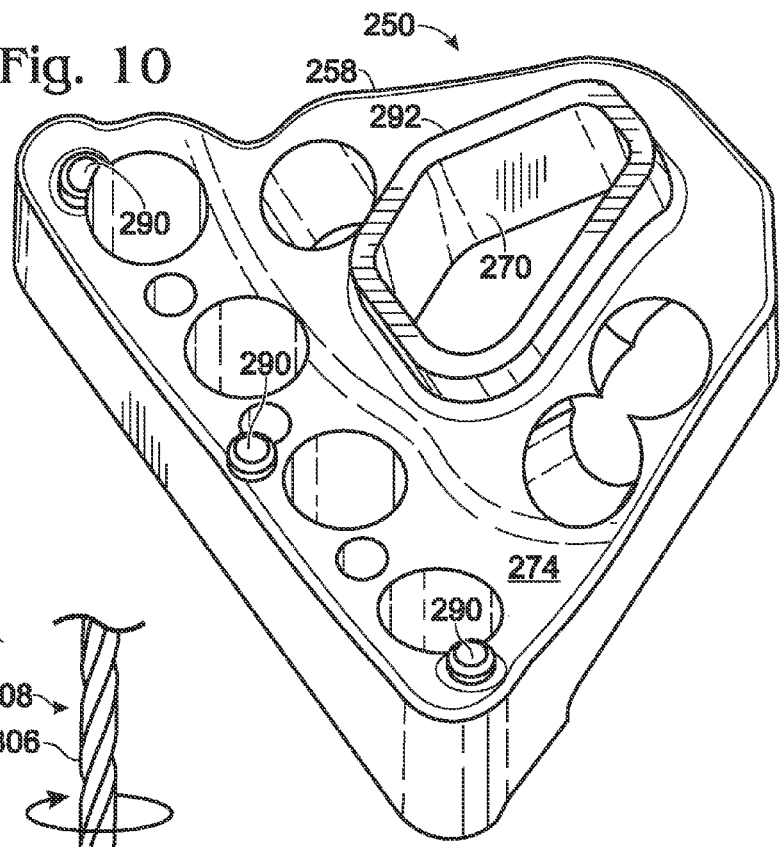
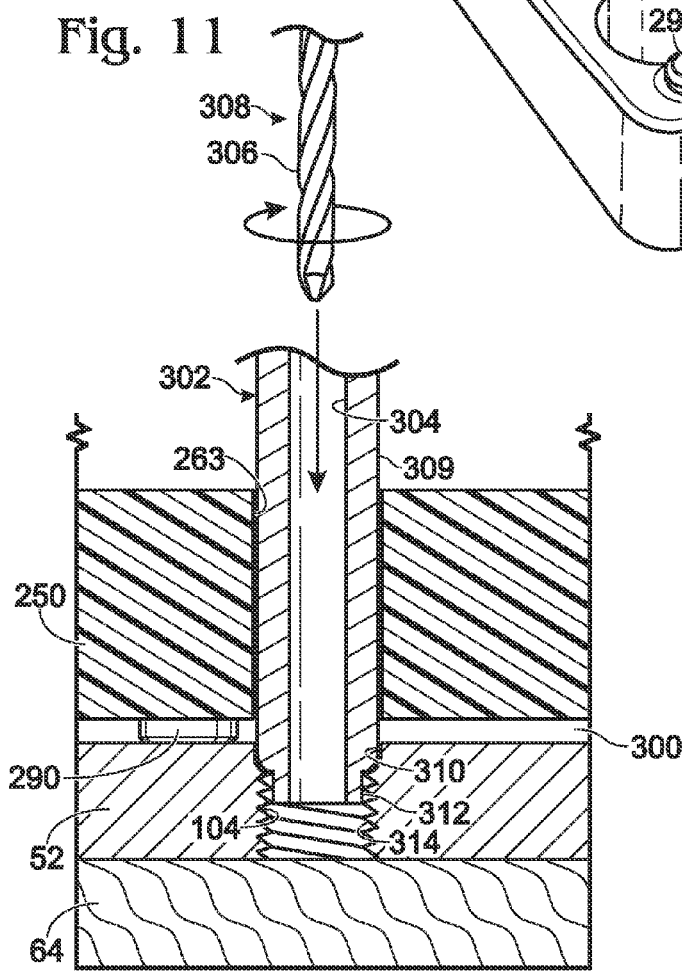

TARGETING GUIDE WITH A RADIOPAQUE MARKER TO FACILITATE POSITIONING A BONE PLATE ON BONE

CROSS-REFERENCES TO PRIORITY APPLICATIONS

This application is based upon and claims the benefit under 35 U.S.C. §119(e) of U.S. Provisional Patent Application Ser. No. 61/386,921, filed Sep. 27, 2010, and U.S. Provisional Patent Application Ser. No. 61/390,120, filed Oct. 5, 2010, each of which is incorporated herein by reference in its entirety for all purposes.

INTRODUCTION

The radius (or radial bone) is one of two long bones found in the human forearm. The radius, like other bones, is susceptible to a variety of fractures and deformities. For example, distal fractures of the radius are a common result, particularly among the elderly, of forward falls with the palms facing downward. In such falls, force exerted on the distal radius at impact frequently produces dorsal displacement of one or more bone fragments created distal to the fracture site.

Fixation of the fractured radius may be performed by internal fixation with a bone plate. The bone plate may be secured on the volar (or dorsal) surface of the distal radius with fasteners, such as bone screws or K-wires, among others. The volar side of the radius may be more accessible surgically and defines a distal pocket in which a distal portion of the bone plate may be disposed. Accordingly, in some cases, the bone plate may be less obtrusive and may produce less tendon irritation with volar placement, even if the bone plate is thicker and sturdier. Bone plates for fixation of the distal radius on either the volar or dorsal surface may include a narrower body portion disposed more proximally on the radius and a wider head portion disposed more distally.

Precise positioning of the bone plate on the radius (or other bone) may be critical for successful fracture fixation, particularly when the end of the bone is fractured into many pieces. In particular, the trajectory of each bone screw into bone is largely determined (variable-angle screws) or completely determined (fixed-angle screws) by where the plate is positioned on the bone, and thus meticulous placement of the bone plate can make screw installation much easier and more effective. Accordingly, a surgeon may spend more time reducing a fracture and positioning and re-positioning the bone plate on bone, than installing bone screws. For example, in some cases, a surgeon may spend about 45 minutes reducing the fracture and achieving the desired placement of the bone plate on the radius and then only about 15 minutes securing the bone plate with bone screws.

A problem faced by surgeons when placing the bone plate on the bone prior to inserting screws is the tendency for the plate to shift while provisionally attaching it with one or more K-wires or clamps. This leads to errors in plate placement, for example, as a result of the plate pivoting and/or sliding. Errors in plate placement for the distal radius can cause screw trajectories to extend into unintended areas, such as into the joint distally or into soft tissue radially.

Surgeons use X-ray-based radiographic imaging, typically, video imaging (fluoroscopy), to monitor the location of the bone plate as it is being moved around on the bone. In orthopedic fluoroscopy, a beam of radiation travels from an X-ray source along a beam axis (i.e., the viewing axis), through a target region of bone to be imaged, and then to a detector behind the target region that detects X-rays in a detection plane transverse to the beam axis. Differential absorption of the X-rays by the bone, air, and the bone plate produces regions of contrast in the images generated.

Instruments such as forceps or a bone clamp commonly are utilized to hold the bone plate in place during fluoroscopy before provisionally attaching the plate to bone with K-wires or other fasteners. This approach can prove difficult because forceps and bone clamps do not provide a rigid attachment to the plate, so the bone plate may shift in position. Also, surgeons do not want to place their hands in the field of view of the fluoroscope, to avoid exposure to X-rays. As a result, manual engagement of the bone plate during fluoroscopy is generally not preferred.

It can be difficult to align the bone plate with features of the bone to achieve optimal plate position. One approach is to align a long axis of the bone plate with the long axis of the shaft of the bone. However, the bone plate may be relatively short and the bone may be wide and tapered where the bone plate is placed, which makes alignment of the plate and bone axes inaccurate.

Handles have been developed to facilitate positioning or stabilizing a bone plate or an associated instrument, such as a guide device, for the bone plate. However, the handle generally is not designed properly to enable fluoroscopy-guided positioning and re-positioning of a bone plate on a target bone, and attachment of the bone plate when situated properly. For example, the handle may be unsuitable for fluoroscopy because the handle is designed to be grasped too close to the plate, which places the surgeon's hand in the field of view and/or exposes the surgeon's hand to excess radiation. Also, the handle may obscure or otherwise interfere with fluoroscopic viewing of the bone plate. Furthermore, the handle may fail to provide suitable orientation features that enable a surgeon to select an informative fluoroscopic view of the bone plate and bone with confidence. The handle also may fail to offer any alignment features for use when checking or adjusting the alignment of the bone plate with bone, particularly if the handle is formed of plastic, which is generally radiolucent. Finally, the handle may obstruct apertures of the bone plate, which prevents placement of fasteners through the obstructed apertures while the handle is attached.

Plate position can determine screw trajectories from apertures of the bone plate into bone. However, surgeons can have difficulty predicting how plate position will relate to screw trajectory without installing screws. One approach for determining prospective screw trajectories is to provisionally attach the plate to bone, and then place wires through apertures of the plate and into bone. The trajectories of the wires can be visualized by fluoroscopy, which indicates the prospective paths of bone screws placed coaxially with the wires. If the wire trajectories are acceptable, cannulated bone screws can be installed over the wires. However, if they are not acceptable, the wires must be removed, the plate re-positioned, and then the wires re-installed to check the new trajectories. This trial-and-error approach can be slow and frustrating to the surgeon, and may damage bone and the joint.

A related trial-and-error approach may be used to place distal screws in a distal row of apertures of a bone plate for the distal radius. A surgeon may have difficulty determining how far distally to place the bone plate on the volar bone surface. Distal screws should be introduced close to the distal articular surface, while being certain that no distal screws intersect the radiocarpal joint distally, the distal radioulnar joint ulnarly, or extend too far radially into soft tissue. A common method used to assess prospective screw placement distally is to place K-wires through small holes in the plate and into bone to define axes that are coplanar with the most distal side of prospectively installed distal screws, then view the wrist under fluoroscopy in a lateral to medial direction to determine if the K-wires are passing into the joint or extend safely into bone. If an adjustment to plate position is needed, the K-wires are removed, the plate position changed, and the K-wires re-installed and re-checked by fluoroscopy. This approach, like the related approach described in the preceding paragraph, can be time-consuming and frustrating for the surgeon and damaging to bone.

The bone plate also may be secured with an obliquely-oriented styloid screw(s) that extends into the radial styloid and locks to the plate at a fixed angle. Typically, distal screws are placed into the more distal apertures of the bone plate before the styloid screw is installed. Accordingly, if the styloid screw trajectory is undesirable, the plate cannot be shifted in position to correct the styloid screw trajectory without taking out all of the distal screws. The surgeon thus may be forced to place a shorter screw or no screw into the radial styloid.

Instruments are needed to facilitate positioning a bone plate on bone under fluoroscopy.

SUMMARY

The present disclosure provides a bone fixation system, including methods, apparatus, and kits, and comprising a bone plate and at least one instrument that attaches to the bone plate and provides at least one radiopaque region to facilitate positioning the bone plate on bone visualized by radiographic imaging. The instrument may be a handle assembly and/or a targeting guide.

BRIEF DESCRIPTION OF THE DRAWINGS

FIG. 1 is a top fragmentary view of selected aspects of an exemplary bone fixation system including a bone plate attached to a targeting guide and a handle assembly, with the bone plate disposed on a distal volar surface region of a radial bone, shown in phantom outline, in accordance with aspects of the present disclosure.

FIG. 2 is an isometric view of the bone fixation system of FIG. 1 with the radial bone not shown.

FIG. 3 is a side elevation view of the bone fixation system of FIG. 1 with the radial bone not shown.

FIG. 4 is a top view of the bone plate of FIG. 1, taken as in FIG. 1 with the bone plate on a distal volar surface region of a fractured radial bone, but with the targeting guide and handle assembly removed, and after attachment of the bone plate to the radial bone with a bone screw received in a styloid aperture of a head portion of the bone plate, in accordance with aspects of the present disclosure.

FIG. 5 is a fragmentary cross-sectional view of the bone fixation system of FIG. 1, taken generally along line 5-5 of FIG. 1 through the bone plate and the handle assembly.

FIG. 6 is a top view of the bone fixation system of FIG. 1, taken as in FIG. 1 with the bone plate on a distal volar surface region of a radial bone and assembled with the targeting guide but with a guide fastener and the handle assembly removed.

FIG. 7 is an exploded view of the targeting guide of FIG. 1, taken generally from above and to the side of the targeting guide.

FIG. 8 is a somewhat schematic side view of the targeting guide of FIG. 6, taken generally along line 8-8 of FIG. 6.

FIG. 9 is another somewhat schematic side view of the targeting guide of FIG. 6, taken along a line that is skewed slightly from line 8-8 of FIG. 6.

FIG. 10 is a bottom view of the targeting guide of FIG. 6.

FIG. 11 is a fragmentary sectional view of the radial bone, bone plate, and targeting guide of FIG. 6, taken generally along line 11-11 of FIG. 6 after placement of a guide tube into one of the openings of the targeting guide, and with a drill bit about to be received in the guide tube, in accordance with aspects the present disclosure.

DETAILED DESCRIPTION

Figure 12:
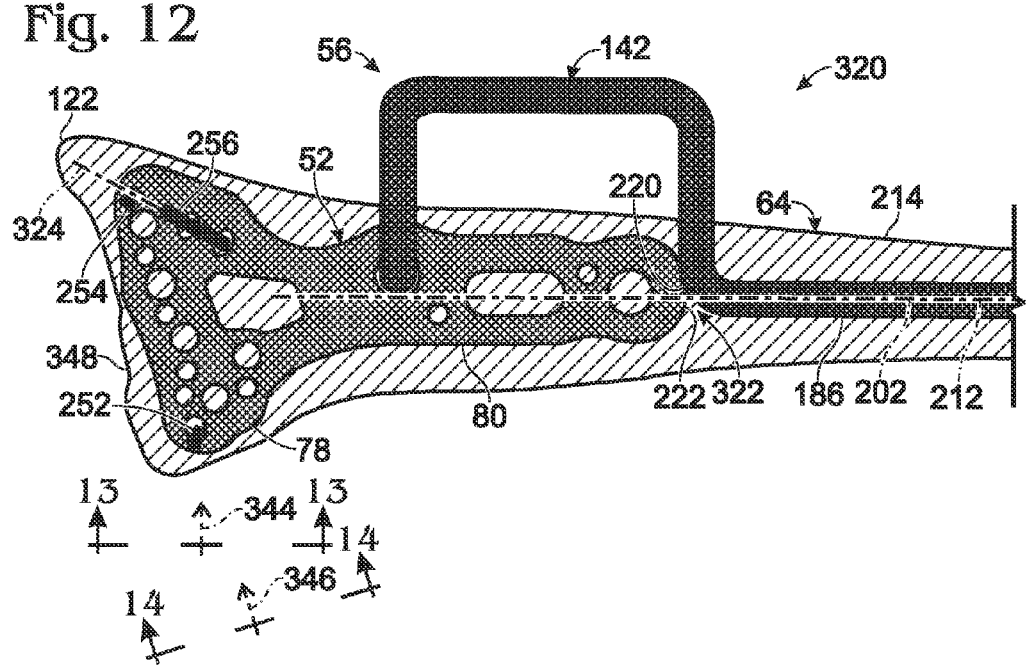
FIG. 12 is a somewhat schematic representation of an exemplary radiographic image of the bone fixation system and radial bone of FIG. 1 that may be generated by fluoroscopy using a radiation beam having a beam axis that is orthogonal to a plane defined by the bone plate, in accordance with aspects of present disclosure.

The present disclosure provides a bone fixation system, including methods, apparatus, and kits, and comprising a bone plate and at least one instrument that attaches to the bone plate and provides at least one radiopaque region to facilitate positioning the bone plate on bone visualized by radiographic imaging. The instrument may be a handle assembly and/or a targeting guide.

An exemplary bone fixation system is provided. The system may comprise a bone plate including an outer surface region and defining a plurality of apertures for receiving fasteners that secure the bone plate to bone. The system also may comprise a guide block attached or attachable to the bone plate with the guide block directly above the outer surface region of the bone plate such that openings of the guide block are adjacent to and in coaxial alignment with apertures of the bone plate. The guide block may include a radiolucent body that defines the openings and also may include at least one elongated, radiopaque marker affixed to the radiolucent body.

Another exemplary bone fixation system is provided. The bone fixation system may comprise a bone plate including a head portion and an elongated body portion. The head portion may have an outer surface and may define a plurality of apertures for receiving fasteners that secure the bone plate to bone. The bone fixation system also may comprise a guide block attached or attachable to the bone plate with the guide block directly above the outer surface region of the head portion such that openings of the guide block are adjacent to and in coaxial alignment with apertures of the head portion. The guide block may include a one-piece, radiolucent body that defines the openings and also may include at least one elongated, radiopaque marker affixed substantially permanently to the radiolucent body.

An exemplary method of bone fixation is provided. In the method, a bone plate may be disposed on a bone. The bone plate may include an outer surface region and may define a plurality of apertures. One or more radiographic images may be generated of the bone, with the bone plate disposed on the bone and attached to a guide block, with the guide block over the outer surface region such that openings of the guide block are adjacent to and in coaxial alignment with the apertures of the bone plate. The guide block may include a radiolucent body that defines the openings and at least one elongated, radiopaque marker disposed in and affixed to the radiolucent body. A position of the bone plate may be adjusted on the bone based on a position of the at least one marker with respect to the bone in the radiographic image. The bone plate may be secured to the bone.

The targeting guide, structured as a guide block, may be perforated to define a plurality of openings through which bone may be drilled and/or fasteners may be placed. The targeting guide may be configured to be assembled with the bone plate, with the openings in coaxial alignment with apertures of the bone plate. In some embodiments, the bone plate may include an outer surface region over which the targeting guide is attached to the bone plate. The outer surface region may be provided by a portion of the bone plate, such as one of a pair of anchor portions. The anchor portion may be a distal portion of a bone plate and/or a head portion of a bone plate including the head portion and a stem portion.

The guide block may include a perforated block or body and one or more markers attached to the body. Each marker may be disposed in the body, for example, such that at least a majority (or at least substantially all) of the marker is contained by the body. In other words, the marker may not project substantially above and/or below the targeting guide. Each marker may be a pin. The body and the markers may differ in their radiopacity (i.e., the extent to which they block ionizing radiation) and thus in their ability to be visualized by imaging with ionizing radiation, generally X-rays. For example, the body of the guide may be radiolucent, while the markers may be relatively radiopaque. Accordingly, with this arrangement, the markers may be readily visible in X-ray images because they contrast with the guide body, and, optionally, with the bone plate.

Each marker may have any suitable disposition with respect to the targeting guide and/or attached bone plate. For example, the targeting guide may include a pair of markers that collectively define a proximal-distal boundary plane through bone to indicate the distal extent of prospectively placed distal bone screws and/or that indicate medial and lateral boundaries for prospective placement of the distal screws in bone. Alternatively, or in addition, the targeting guide may include a marker that forms a line segment in an X-ray image taken orthogonal to the outer surface region of the bone plate. The line segment may be oriented obliquely to the long axis and a width axis of the bone plate, and/or may point to an anatomical landmark on the bone in a radiographic image when the bone plate is correctly positioned on the bone.

An exemplary method of bone fixation is provided. In the method, a handle assembly may be fastened to a bone plate defining a long axis. The handle assembly may include an extension portion connected to a graspable grip portion. The extension portion may provide a radiopaque alignment region that is offset from the bone plate along the long axis. One or more radiographic images may be generated of the alignment region disposed above a shaft portion of a long bone while the bone plate is disposed on an end portion of the long bone that is wider than the shaft portion. An orientation of the bone plate on the long bone may be adjusted based on a relative alignment of the alignment region and the shaft portion in the radiographic images. The bone plate may be secured to the long bone. The handle assembly may be disconnected from the bone plate.

Another exemplary method of bone fixation is provided. In the method, a bone plate may be selected. The bone plate may include a head portion connected to an elongated body portion. The body portion may be narrower than the head portion and may define a plane and a long axis. A handle assembly may be fastened to the bone plate. The handle assembly may include an extension portion connected to a graspable grip portion. The extension portion may provide a radiopaque alignment region that is offset from the bone plate along the long axis in a direction away from the head portion. Radiographic images of the alignment region disposed above a shaft portion of a long bone may be generated while the bone plate is disposed on an end portion of the long bone and using a beam of radiation having a beam axis oriented substantially orthogonal to the plane of the bone plate. The alignment region may be positioned to be substantially parallel to the shaft portion of the long bone in one or more of the radiographic images. The bone plate may be secured to the long bone. The handle assembly may be disconnected from the bone plate.

Yet another exemplary method of bone fixation is provided. In the method, a bone plate and a handle assembly may be selected. The bone plate may include a head portion connected to an elongated body portion. The body portion may be narrower than the head portion and may define a long axis. The handle assembly may include a base portion, a graspable grip portion, and an extension portion connecting the grip portion to the base portion. The extension portion may provide a radiopaque alignment region. The bone plate may be fastened to the handle assembly at the base portion with at least one threaded fastener. The bone plate may be disposed on end portion of a long bone and the alignment region above a shaft portion of the long bone, with the alignment region and the shaft portion defining respective long axes that are substantially coplanar to each other. The bone plate may be secured to the long bone. The handle assembly may be disconnected from the bone plate.

The handle may be rigidly attachable to the bone plate and, due to its length and shape, may allow a surgeon to make precise changes in plate position on bone prior to provisional or final fixation with K-wires and/or screws. The handle also may permit the surgeon to manipulate the bone plate remotely, with less X-ray exposure to the surgeon's hands during fluoroscopy, because the grasped portion of the handle is outside the fluoroscopic field. Also, the handle may enable better and quicker alignment of the bone plate with bone, easier determination of whether the fluoroscopic view is orthogonal to the bone plate and/or transverse to the bone (e.g., medial-lateral) or bone plate, and installation of one or more fasteners where the handle may be laterally offset from the bone plate. The same handle also may be designed to clear soft tissue and the incision when used on right or left plates.

Further aspects of the present disclosure are described in the following sections: (I) overview of an exemplary bone fixation system, (II) exemplary bone plate, (III) exemplary handle, (IV) exemplary targeting guide, (V) composition of system components, (VI) methods of bone plate positioning, attachment to bone, and bone fixation, (VII) kits, and (VIII) examples.

I. Overview of an Exemplary Bone Fixation System

FIGS. 1-3 show various views of an exemplary bone fixation system 50 including a bone plate 52 fastened to a targeting guide 54 and a handle 56 (also termed a handle assembly) using respective fasteners 58, 60. Guide 54 and handle 56 may function as instruments that each provide at least one radiopaque region to facilitate positioning the bone plate on a bone visualized by radiographic imaging. The guide and/or handle also or alternatively may be used to facilitate placement of fasteners into bone and/or for holding and moving the bone plate, among others.

The bone fixation system, and particularly bone plate 52, may be disposed on a bone 62. In FIG. 1, bone 62 is shown in phantom outline and is a long bone, namely, a radial bone 64. Bone plate 52 may, for example, be disposed on a distal volar (or dorsal) surface region 66 of radial bone 64. However, the fixation system may be configured for use with any suitable bone.

In any event, the bone plate may be placed on the bone, and the position of the bone plate determined and/or inferred by radiographic imaging, such as fluoroscopy, with the aid of one or more radiopaque regions of guide 54 and/or handle 56. The bone plate may be re-positioned on the bone if desired, based on one or more radiographic images that show the radiopaque region(s), and optionally by manipulating handle 56. Fasteners then may be installed, optionally with the aid of targeting guide 54, to secure the bone plate to bone. For example, the targeting guide may be used directly to guide a drill bit, a fastener, and/or driver and/or may be utilized to hold one or more guide tubes that guide a drill bit, a fastener, and/or a driver, among others. In any event, each of guide 54 and handle 56 may be disconnected from the bone plate and removed after (or before) the bone plate is secured to bone. Further aspects of the radiopaque regions of the guide and handle and their use in bone plate installation are described below.

II. Exemplary Bone Plate

FIG. 4 shows bone plate 52 disposed an end portion of a bone, namely, on volar surface region 66 of a distal part of radial bone 64. The bone plate may be attached to the bone with fasteners, such as bone screws, but to simplify the presentation, only one bone screw 70 is shown here. Guide 54 and handle 56 have been disconnected and removed.

The bone plate may have a proximal portion 72 connected to a distal portion 74, with the proximal and distal portions arranged along the bone plate from each other. In use, each of the proximal and distal portions of the bone plate may function as anchor portions disposed on opposing sides of a bone discontinuity, such as a fracture 76, with the bone plate spanning the discontinuity. The proximal and distal portions of the bone plate may provide respective attachment sites for targeting guide 54 and handle 56. Also or alternatively, the bone plate may have a relatively wider head portion 78 connected to a relatively narrower, elongated body portion 80. The head portion may be configured to be disposed distal to the body portion on bone, or vice versa.

The bone plate or a portion thereof may define a long axis 82. In bone plate 52, body portion 80 defines long axis 82. The bone plate may bend upward or downward, away from the long axis as it extends longitudinally. For example, bone plate 52 bends upward from long axis 82 as it extends from the body portion to the head portion (e.g., see FIG. 3). Body portion 80 and/or an inner and/or outer surface region 83, 84 thereof may define a plane 86 (see FIG. 5), such as a center-of-mass plane for the body portion that contains long axis 82. The plane may be at least generally parallel to inner and outer surface regions 83, 84 of the body portion and/or may be at least generally tangential to inner surface region 83 or outer surface region 84. An orthogonal plane 88 may contain long axis 82 and be orthogonal to plane 86 (see FIG. 5), to conceptually divide body portion 80 and/or bone plate 52 into at least approximate halves.

The bone plate may have an inner surface region 90 (see FIGS. 3 and 5) that is contoured to substantially match a surface region of a target bone such that the bone plate fits onto the bone. The head portion of the bone plate may provide the contoured inner surface region. In some cases, head portion 78 may provide an inner surface region contoured to substantially match and/or fit onto a distal surface region of a radial bone or a tibial bone, among others. The inner surface region may, for example, function as a template to assist a surgeon in bone reconstruction near the end of a bone, such as when the bone is fragmented into several or more pieces.

Bone plate 52 may define a plurality of apertures of the same or different size (see FIG. 4). Each aperture may or may not include locking structure, such as an internal thread, to lock a fastener to the aperture. Also, each aperture may be used with a toggle fastener or a fixed-angle fastener. The apertures may include apertures 102-116 defined by head portion 78 and body portion 80 of the bone plate to receive narrower and wider bone screws, respectively. Aperture 110 may be configured to receive styloid screw 70 that extends into radial styloid 122 of the radial bone. Aperture 116 additionally may be utilized to provide threaded engagement of handle fastener 60 with the bone plate (see FIGS. 4 and 5), and any of apertures 102-114 may be utilized for the same purpose with guide fastener 58 (e.g., see FIG. 1). The bone plate also may include smaller apertures 124 to receive wires. The bone plate further may define at least one elongate aperture or slot 126 to facilitate plate repositioning when the bone plate is connected to bone only with a screw in aperture 126 and/or to provide compression. The bone plate also may define an access port 128 to facilitate manipulation of underlying bone, such as movement of bone fragments and/or addition of a bone graft through the port. The access port also may be used to facilitate mating of bone plate 52 with guide 54, as described below in Section IV.

The bone plate may be equipped with a provisional or interim retainer or cleat 130 that protrudes from an inner surface of bone plate 52. The cleat may be continuous with a plate body that forms the inner surface, that is, the cleat may be formed integrally or monolithically with the plate body. The cleat may taper away from the plate body and may be at least generally pointed in profile, to form a prong. In any event, the cleat may be configured to permit bone plate 52 to slide on bone (e.g., with guide 54 and handle 56 attached; see FIG. 1) until the cleat is urged against bone, to provide an anti-slip function until a provisional fastener can be installed to better stabilize bone plate position. The cleat may slide along a surface region of bone with the bone plate, while the bone plate is being moved into a desired position on bone, and then may form and occupy an indentation in bone to stabilize the current plate position, by resisting plate slippage. The cleat may be urged into bone by applying pressure to the bone plate toward bone using a surgeon's hand (e.g., pushing on the bone plate with a finger or thumb), with a separate tool, with handle 56, or the like. The cleat may be miniature in size, which may avoid a substantial effect on how the bone plate fits and slides on bone before the cleat is urged into bone, may minimize damage to bone, and/or may facilitate removing the cleat from bone when the plate is to be moved. The miniature cleat may project from the body of the bone plate by substantially less than the thickness of the bone plate, such as less than about one-half the thickness of the bone plate. Further aspects of an exemplary cleat that may be suitable are described in U.S. Provisional Patent Application Ser. No. 61/390,120, filed Oct. 5, 2010, which is incorporated herein by reference.

III. Exemplary Handle

FIGS. 1-3 and 5 show various aspects of handle 56. The handle may include an attachment or base portion 140, an extension portion 142, and a graspable grip portion 144, among others.

Base portion 140 may include a bracket 146 that engages bone plate 52 (see FIGS. 1-3 and 5). The base portion and/or bracket 146 may be at least generally U-shaped. Base portion 140 may define one or more openings 148-154 that overlap and/or are co-axial with apertures of the bone plate (see FIG. 1).

Fastener 60 may be received in opening 148 to attach handle 56 to bone plate 52 (see FIG. 5). The handle fastener may have an external thread 160 formed near its distal end for threaded engagement with an internal thread of aperture 116 of bone plate 52 (also see FIG. 4). A shoulder 162 may be formed proximal to the external thread. The shoulder may act as a stop that engages bracket 146 adjacent opening 148, to block threaded advancement of fastener 60 into the bone plate. A proximal shaft 164 may extend to a graspable head 166 of the fastener that provides a knurled surface 168 to resist slippage during manual engagement. Fastener 60 (and/or fastener 58) may be described as a thumbscrew, namely, a threaded fastener configured to be turned by hand.

Handle 56 may be configured to be attached to both left-side and right-side versions of bone plate 52 (to fix left and right radial bones), using handle fastener 60. Accordingly, base portion 140 may be designed to provide alignment of openings 148-154 (see FIG. 1) with bone plate apertures of both left and right versions of bone plate 52. In particular, any of the openings of the base portion may be elongated (e.g., opening 148) or duplicated (e.g., openings 150 and 152) to accommodate lateral shifts in the position of non-centered apertures (e.g., aperture 116) between left and right bone plates. Opening 148 may have a keyhole shape that permits handle fastener 60 to be retained in the narrower portion of the keyhole whether or not the fastener is attached to the bone plate.

Bracket 146 may define a socket 170 to receive an end of extension portion 142 of the handle. The extension portion may be affixed to the bracket in the socket.

The inner surface of bracket 146 may define a cavity 172 to receive a region of the bone plate. Thus, the base portion and bone plate may have complementary engagement surfaces for mating with one another.

Extension portion 142 may extend from base portion 140 to grip portion 144 (see FIGS. 1-3). The extension portion may be described as a stem or a shaft, which connects to a head (grip portion 144). The extension portion may extend along a nonlinear path, which may bend at least once or two or more times, at least generally above and to a position longitudinally beyond an end of the bone plate. The extension portion may form an elevation region 180 extending upwardly and, optionally, obliquely (e.g., in a lateral direction) from the bone plate and also may form an offset region 182, which may extend parallel to long axis 82 of the bone plate (see FIG. 1) but not directly above the long axis (i.e., laterally offset from the bone plate). The extension portion further may form a transverse region 184 extending back to a position directly above the bone plate, an alignment region 186, and a grip interface region 188, among others. A first structure that is "directly above" a second structure is arranged above the second structure on a vertical or orthogonal axis that extends from the second structure to the first structure, with or without at least one other structure disposed between the first and second structures.

Any suitable region or all of extension portion 142 may be radiopaque to permit radiographic visualization, such as by fluoroscopy. For example, transverse region 184 and/or alignment region 186 may be radiopaque. In exemplary embodiments, extension portion 142 may be formed of metal, such as stainless steel. The extension portion may be a bent cylinder and/or at least generally round in cross-section. Also, the alignment region may be cylindrical. In some embodiments, a body of the extension portion may be formed of a radiolucent material, such as plastic, having a radiopaque insert (e.g., an embedded metal wire) or covering (e.g., a metal sleeve).

The term "radiopaque" means relatively efficient at blocking X-rays. A structure that is radiopaque is formed of a material that is better at blocking X-rays than bone and generally contrasts with overlapped bone in radiographic images. The term "radiolucent" means substantially less efficient at blocking X-rays than something that is radiopaque. A structure that is radiolucent may be formed of a material that does not block X-rays as well as bone and may be less visible than bone (and/or substantially invisible relative to overlapped bone) in radiographic images.

Handle 56 may be structured to define one or more axes that are parallel to one or more characteristic axes defined by the bone plate (see FIGS. 1-3). For example, the handle may define a shaft-alignment axis 200 oriented parallel and/or coplanar to long axis 82 defined by the bone plate, and/or parallel to and/or disposed in orthogonal plane 88. Also, the handle may define a transverse axis 202 oriented parallel to a width axis 204 (another transverse axis) defined by the bone plate. Further, the handle may define a z-axis 206 oriented parallel to a height or thickness axis of the bone plate. Z-axis 206 may be defined as an axis that is positioned at a junction 210 of transverse region 184 and alignment region 186 and that is mutually orthogonal to shaft-alignment axis 200 and transverse axis 202 (see FIG. 2). Accordingly, the handle may define a set of orthogonal axes related translationally to characteristic axes of the bone plate. Each of axes 200, 202, 206 may be assignable in a radiographic view of the handle alone and/or the handle attached to the bone plate.

Alignment region 186 may (or may not) be substantially narrower than the bone plate. For example, the alignment region may be no more than about one-half or one-fourth as wide as body portion 80 of the bone plate, which may be closest to the alignment region. A relatively narrow alignment region may be advantageous to reduce weight and cost, to minimize obstruction of other structures (e.g., bone, the bone plate, and fasteners) during fluoroscopy, and to define a more clearly discernable alignment axis.

The alignment region may be elevated with respect to body portion 80 and offset from body portion along long axis 82 in a direction away from head portion 78. Alignment region 186 may be offset any suitable distance such as at least about one-half the length of the alignment region.

A typical long bone, such as radial bone 64, is relatively wider near its proximal and distal ends. Accordingly, a surgeon may have difficulty determining whether a bone plate placed on an end portion of a long bone is aligned with the shaft of the bone. Alignment region 186 may be used to facilitate alignment of the long axes of the bone plate and the bone, for example, alignment of long axis 82 defined by body portion 80 of the bone plate with a long axis 212 defined by a shaft portion 214 of the bone (see FIG. 1). For this purpose, the bone may be viewed fluoroscopically using a beam axis that is orthogonal to bone plate 52 (e.g., with the bone viewed parallel to axis 206 (see FIGS. 2 and 3), such as in an anterior-posterior view (see FIG. 1)). Alignment region 186 may be disposed more centrally along the bone relative to the bone plate, such that the alignment region is above a narrower region of the bone. Use of the alignment region above a narrower region of the bone allows the surgeon to more easily and accurately determine whether the alignment region is centered over the bone shaft.

Alignment region 186 may be elevated above bone and thus with respect to bone plate 52 (e.g., see FIGS. 2 and 3). Accordingly, views of the bone plate and the alignment region taken obliquely to bone plate 52, particularly skewed from orthogonal to plate 52 about an axis parallel to long axis 82, do not position the alignment region and the bone plate coaxial to each other in radiographic images. (If alignment region 186 is parallel to long axis 82, region 186 and the bone plate may be parallel and laterally offset from each other if the view is skewed.) To ensure proper orientation of the beam axis to provide a view orthogonal to the bone plate, the bone plate and handle may form a radiographically visible juxtaposition of a landmark 220 of extension portion 142 with an edge feature 222 of bone plate 52, to signify that the beam axis is substantially orthogonal to the plane of the bone plate (see FIG. 1 and Ex. 1). Here, landmark 220 is junction 210 formed by a bend (e.g., a right-angle bend) where transverse region 184 and alignment region 186 meet (see FIG. 2). More generally, landmark 220 may be a bend in the extension portion, a change in width of the extension portion, an aperture of the extension portion, or a combination thereof, among others. In any event, the landmark may be formed along extension portion 142 at a position that is directly above edge feature 222 of the bone plate. The edge feature may be a site on the outer edge of the bone plate (forming a perimeter of the bone plate) or a site on one of a plurality of inner edges that bound apertures of the bone plate. In the present illustration, landmark 220 is configured to be superimposed, in radiographic images, on edge feature 222 formed at one end of the bone plate. In use, a surgeon may adjust the position of the bone (and/or the beam axis) until landmark 220 of handle 56 and edge feature 222 of bone plate 52 are close or overlap in radiographic images, to ensure a substantially orthogonal view (or other predefined view) of the bone plate (and/or bone).

Handle 56 may travel a circuitous route from base portion 140 to alignment region 186, particularly if base portion 140 is disposed on a longitudinally central region of the bone plate. In particular, offset region 182 may be offset laterally above the bone plate, rather than being positioned directly above the bone plate (e.g., see FIG. 1). The offset region thus may follow a path that avoids obstructing apertures of the bone plate, which permits fasteners to be placed into the apertures while the handle is still attached. For example, a surgeon may place a bone screw through aperture 118 or slot 126 (see FIG. 4) while the handle remains attached to the bone plate. Attachment of the handle to the central region of the bone plate (e.g., via bone plate aperture 116), rather than near the end of the bone plate, may be advantageous to minimize the length of the incision and/or to provide finer control over bone plate position via handle manipulation.

FIG. 3 shows a side view of the bone fixation system 50, taken parallel to transverse axes 202, 204 defined by the bone plate and the handle (see FIG. 1). At least two of offset region 182, transverse region 184, and alignment region 186 may define coplanar axes, which collectively define a plane. In FIG. 3, the plane defined by these coplanar axes is oriented orthogonally to the plane of view. In any event, the positions of any of these regions may be used by a surgeon during fluoroscopy to select a transverse view of the bone plate, such as by adjusting the beam axis until transverse region 184 is viewed end-on. Accordingly, regions 182-186 may be used to, for example, facilitate generating an accurate medial-lateral view of the radial bone during fluoroscopy.

Grip portion 144 may be sized to be grasped by a person's hand (gloved or ungloved). Accordingly, the grip portion may be substantially wider than extension portion 142 of the handle, such as at least about 2, 3, or 5 times wider. The grip portion may be disposed in a longitudinally spaced and elevated relation to the bone plate, such that the grip portion (and a hand grasping the grip portion) can stay away from the X-ray beam of an imaging device during use of the handle. Thus, the grip portion may be disposed above an intact region of skin at a position remote from the bone plate during use. In other words, the handle may provide clearance above soft tissue when the handle is being utilized to position the plate. The grip portion may be connected to extension portion 142 by any suitable mechanism, such as a set screw, a press fit, threaded engagement, an adhesive, bonding, or the like.

IV. Exemplary Targeting Guide

FIGS. 6 and 7 show respective intact and exploded views of targeting guide 54. In FIG. 6, bone plate 52 is assembled with guide 54 on radial bone 64, as in FIG. 1, but handle 56 and fasteners 58, 60 are not shown. In this view, guide 54 is disposed over an outer surface region 240 of head portion 78 of bone plate 52, with the guide substantially covering the head portion and in contact with outer surface region 240. The guide may be disposed selectively over the head portion relative to the body portion of the bone plate.

Targeting guide 54 may be structured as a guide block 250 equipped with one or more radiographic markers 252-256 attached to a perforated body 258. The body may be a single piece. The markers may be used via radiographic imaging, such as during fluoroscopy, to check, monitor, and improve the position of a bone plate on bone.

Body 258 may define a plurality of openings that correspond in size and position to apertures of the bone plate. (The terms "opening" and "aperture" are interchangeable in the present disclosure.) The openings may be collectively arrangeable in coaxial alignment with apertures of the bone plate. In the present illustration, the openings are sized in correspondence with, and arrangeable in coaxial alignment with apertures 102-114, smaller holes 124, and access port 128 of head portion 78 of bone plate 52 (compare FIG. 4 with FIGS. 6 and 7). For example, smaller distal openings 260 of the guide block (see FIG. 7) may be aligned with smaller distal apertures 124 of the bone plate (see FIG. 4), to allow placement of wires through the guide block and the bone plate. Also, larger openings 262-268 of the guide block may assist in guiding a drill bit and/or a bone screw into aligned bone plate apertures, such as by receiving and holding a guide tube. The larger openings may include distal openings 262-265 that facilitate installation of distal fasteners in a row of distal apertures 102-108, respectively. The larger openings also may include an ulnar opening 266, and dual styloid openings 267, 268 that are contiguous and facilitate installation of styloid screw 70 and another screw through apertures 110, 112 and into the radial styloid (see FIGS. 4 and 7). The guide block further may be equipped with a largest opening 270 that corresponds in size, shape, and position to access port 128 of the bone plate.

Each marker may be affixed to the body before the guide block is attached to the bone plate. Each marker may be integral to the guide block, meaning that the marker is disposed in and affixed substantially permanently to body 258 such that the marker cannot be removed readily from the guide block. The marker may be contained at least substantially (or completely) in the body. For example, the marker may not project substantially (or at all) from an outer surface 272 and/or an inner surface 274 of body 258 (see FIGS. 7 and 8). A marker that does not project substantially projects by a distance that is no more than about 20% or 10% of the thickness of the body and/or has less than about 20% or 10% of the marker's total length projecting from the body. In any event, the marker may remain completely outside bone during use.

Each marker may be radiographically distinguishable from body 258, such that the marker is visible in radiographic images (e.g., collected by fluoroscopy). For example, the marker may be radiopaque and the body radiolucent, or vice versa. In exemplary embodiments, the marker may be formed of metal and the body of plastic. In some embodiments, the body may be radiopaque (e.g., formed of metal) and the marker(s) may be radiolucent and formed by at least one opening or radiolucent insert in the body.

Each marker may extend adjacent to at least one opening of guide block 250. However, the marker may not be co-axial with any of the guide openings that accept bone screws. The marker and its adjacent, corresponding opening may define respective axes that are substantially parallel to and spaced from each other or substantially coplanar to each other, among others. In any event, with a suitable radiographic view, the marker may allow a surgeon to predict a prospective fastener trajectory into bone. The use of a targeting guide with one or more radiopaque markers may permit the prospective trajectories of one or more fasteners to be predicted more quickly, via fluoroscopy, as the bone plate is being positioned on bone, and without the need for the labor-intensive and time-consuming insertion of K-wires to define prospective trajectories.

Each marker may be received in a hole 276 formed in body 258 (see FIG. 7). The hole may, for example, be a blind hole that is open at the top (or the bottom) of guide body 258. During guide construction, the marker may be placed into the hole and held in place therein by any suitable mechanism. For example, the marker may be press-fitted, secured with an adhesive or by bonding, held by threaded engagement with the body or by swaging the body around/over the marker, or the like. In any event, the marker may be attached such that the marker is fixed to the guide body.

The marker may be elongate and may have a diameter that is less than that of larger openings of the guide block (e.g., openings 262-268). For example, the marker may have a diameter of less than about 2 mm or 1 mm, among others. In other words, the marker may have a diameter corresponding to that of a K-wire. The marker may be substantially cylindrical and/or linear and may have chamfered ends to facilitate placing the marker into the body and/or swaging the body over/around the end of the marker during construction of the guide block. The marker may be described as a pin and/or a post.

The guide block may include any suitable number of markers. Here, three markers are shown. A pair of distal markers 252, 254 are parallel to one another and parallel to distal small openings 260 and to a row of larger distal openings 262-265 of guide block 250. Styloid marker 256 defines an axis 278 that may be coplanar with (and, optionally, parallel to) an axis 280 defined by first styloid opening 267 (and/or second styloid opening 268) of the guide block, through which styloid screw 70 is placed into radial styloid 122 of the distal radius (see FIGS. 4 and 6-8).

FIG. 8 shows a side view of guide block 250. Markers 252, 254 can help a surgeon predict, in fluoroscopic images taken along orthogonal axes, where the entire distal row of bone screws will be implanted in a bone. For example, distal markers 252, 254 may collectively define a distal boundary plane along a proximal-distal axis for a row of distal screws placed into bone along parallel axes, in a linear array, through distal row of apertures 102-108 of the bone plate (also see FIG. 4). These distal markers allow a surgeon, without insertion of K-wires, to quickly determine under fluoroscopy, with a medial-lateral beam axis, whether screws inserted into the bone through distal apertures 102-108 will enter the joint. In other words, the boundary plane indicates, in a radiographic image, whether and/or how closely bone screws placed into distal apertures 102-108 will approach or cross the radiocarpal articular surface of the radial bone. This reduces surgery time by avoiding placement of K-wires to check screw trajectory. Because there are two markers 252, 254 located near the distal ulnar and distal radial corners of the guide (see FIG. 6), these markers also help the surgeon predict the medial and lateral boundaries of screw placement. With a beam axis oriented generally parallel to markers 252, 254, these markers may appear as dots rather than line segments in radiographic images, while styloid marker 256 may appear as a line segment.

Styloid marker 256 may extend obliquely in guide block 250 to enable prediction of the trajectory of styloid screw 70 into radial styloid 122 of radial bone 64 (see FIGS. 4, 6, and 8). Marker 256 can be used during fluoroscopy with, for example, an anterior-posterior beam axis while positioning the plate, such as with handle 56 (e.g., see FIG. 1), to correctly orient the plate with respect to radial styloid 122 prior to securing the plate to bone. In some embodiments, when marker 256 points to the tip of radial styloid 122 in a radiographic image generated with a beam axis orthogonal to the bone plate, the bone plate is positioned correctly and correct styloid screw placement can be ensured. However, any other suitable anatomical landmark(s) on any suitable bone may be used as a target for marker 256. Exemplary landmarks include a process or a fossa, among others.

FIG. 9 shows a side view of guide block 250 taken along an axis that is skewed slightly from that of FIG. 8. The side view is orthogonal to each of distal markers 252, 254 but oblique to a plane defined by these markers. As a result, distal markers 252, 254 are parallel, with ends aligned, but spaced from one another in this view. Accordingly, in a radiographic image collected with the same viewing axis, distal markers 252, 254 would form a pair of line segments with a spacing determined by the angular offset of the viewing angle from the markers' collectively defined plane. Therefore, the shape and relative position (coincident, overlapped, or resolved; offset from each other along their long axes or aligned longitudinally) of distal markers 252, 254 in radiographic images may be used to determine whether the viewing axis is in the intended direction or skewed therefrom.

FIG. 10 shows a bottom view of guide block 250. Inner surface 274 of the guide block and/or guide body 258 may be contoured to be at least generally complementary to outer surface region 240 of the bone plate (also see FIG. 6). Feet 290 may be formed on inner surface 274 to elevate the inner surface slightly from the outer surface region of the bone plate. The guide block may be equipped with at least one mating projection, such as a flange 292, that projects from inner surface 274. The mating projection may be configured to be received in an aperture of the bone plate, to mate the guide block with the bone plate. For example, flange 292 may be shaped, sized, and positioned to be received in access port 128 of the bone plate (also see FIG. 4). Flange 292 may or may not extend around the base of largest opening 270 of guide block 250. In any event, the mating projection(s) may allow the bone plate and the guide block to mate with one another along an axis transverse to the plane of the bone plate, such that the openings of the guide block are adjacent to and correctly aligned with apertures of the bone plate and such that relative pivotal motion of the bone plate and guide block is restricted. The guide block can be fastened to the bone plate using fastener 58 received in any of the larger openings of the guide block and locked to the bone plate (e.g., by threaded engagement with an aperture of the bone plate). Fastener 58 may have any of the features disclosed for fastener 60 (e.g., see FIG. 5).

FIG. 11 shows a sectional view of radial bone 64, bone plate 52, and guide block 250 taken through distal aperture 104 of the bone plate and distal opening 263 of the guide block. The distal aperture and the distal opening may be coaxial to each other and may have about the same diameter. Foot 290 may elevate the guide block from the bone plate to form a gap 300 between the bone plate and the body of the guide block. The gap may be less than (as shown here), about the same as, or greater than the thickness of the bone plate. Also, the thickness of the guide block may be greater than the thickness of the bone plate, such as at least about two or four times greater, among others.

Guide block 250 may receive a guide tube 302 in any of openings 262-268 of the guide block. The opening, such as opening 263 shown here, may help to orient and support the guide tube. Tube 302, which may be described as a cannula, defines a longitudinal through-bore 304, which may be sized to receive a drill bit 306 of a drill 308. The guide tube may have a body 309 that is sized to fit snugly into opening 263 and extend into a counterbore 310 of aperture 104. The guide tube also may have a nose 312 of smaller diameter that is sized to be received in a lower, threaded region 314 of aperture 104.

V. Composition of System Components

The bone plate, targeting guide, handle, and fasteners disclosed herein may be formed of any suitable biocompatible material(s). Exemplary biocompatible materials include (1) metals (for example, titanium or titanium alloys, alloys with cobalt and chromium (cobalt-chrome), stainless steel, etc.); (2) plastics/polymers (for example, ultra-high molecular weight polyethylene (UHMWPE), polymethylmethacrylate (PMMA), polytetrafluoroethylene (PTFE), polyetheretherketone (PEEK), nylon, polypropylene, and/or PMMA/polyhydroxyethylmethacrylate (PHEMA)); (3) ceramics (for example, alumina, beryllia, and/or zirconia, among others); (4) composites (e.g., a polymer matrix (such as PEEK) containing carbon fibers and/or ceramic); (5) bioresorbable (bioabsorbable) materials or polymers (for example, polymers of α-hydroxy carboxylic acids (e.g., polylactic acid (such as PLLA, PDLLA, and/or PDLA), polyglycolic acid, lactide/glycolide copolymers, etc.), polydioxanones, polycaprolactones, polytrimethylene carbonate, polyethylene oxide, poly-β-hydroxybutyrate, poly-β-hydroxypropionate, poly-δ-valerolactone, other bioresorbable polyesters, etc.; and/or the like.

In exemplary embodiments, the bone plate is formed of metal (e.g., titanium or a titanium alloy or stainless steel, among others), the extension portion of the handle is also formed of metal (e.g., stainless steel or titanium alloy, among others), and the targeting guide has a plastic/polymer body carrying one or more metal markers (e.g., titanium, titanium alloy, or stainless steel, among others). The bone plate, handle, and markers may be formed of materials having different radiopacities (i.e., different abilities to block X-rays), such as a bone plate formed of titanium or a titanium alloy, and a handle extension portion and markers formed of stainless steel.

The ability of a given element to block X-rays is generally proportional to its mass cubed. Also, the blocking ability of a structure formed of the element is generally proportional to the intrinsic blocking ability of the element multiplied by the characteristic dimension of the structure measured parallel to the beam axis (e.g., the structure's thickness or width).

VI. Methods of Bone Plate Positioning, Attachment to Bone, and Bone Fixation

The systems disclosed herein may provide a method of bone fixation, situating a bone plate on bone, and/or attaching a bone plate to bone. The method may include any combination of the steps disclosed in this section or elsewhere in the present disclosure, performed in any suitable order.

A bone plate may be disposed on any suitable bone, such as a long bone. Exemplary bones include a bone of the arms (such as a humerus, a radius, and/or an ulna), a bone of the legs (such as a femur, a tibia, and/or a fibula), a bone of the hands (such as a carpal, metacarpal, and/or phalange), a bone of the feet (such as a tarsal, metatarsal, and/or phalange), a clavicle, a rib, a scapula, a pelvic bone, a vertebra, a skull, a mandible, or the like. Particular bones that may be suitable are a distal part or end region of the radius or tibia, among others. The bone may include a discontinuity, such as a fracture, a cut (e.g., as a result of an osteotomy), a deformation, a structural instability, or the like.

A targeting guide and/or a handle may be attached to the bone plate to form a bone plate assembly. Attachment of each component may be performed before or after the bone plate is disposed on the bone. The targeting guide and the handle may be connected to the bone plate as a unit or may be connected as discrete, separate components.

The targeting guide may be disposed over an outer surface region of the bone plate such that openings of the targeting guide are adjacent to and in coaxial alignment with the apertures of the bone plate. The targeting guide may include any of the features disclosed herein. For example, the targeting guide may include a relatively radiolucent body and at least one relatively radiopaque marker attached to the body.

The handle may be connected to the bone plate at any suitable position thereof. For example, the handle may be connected near an end of the bone plate or at a central position intermediate opposing end regions of the bone plate. The handle, when attached the bone plate, may dispose a radiopaque alignment region parallel and/or coaxial to a long axis defined by the bone plate and offset orthogonally and longitudinally from the bone plate. As a result, the alignment region may appear as an axial extension (e.g., a narrower extension) of the bone plate in radiographic images taken with a beam axis oriented orthogonal to the bone plate. The axial extension may overlap or be spaced from the bone plate in the images.

The bone plate, bone, targeting guide, and handle, or any combination thereof, may be imaged radiographically (generally, with X-rays), such as by fluoroscopy. Radiographic images (e.g., one or more X-ray images) may be generated by detection of X-rays. The bone and bone plate assembly may be viewed using a beam axis oriented orthogonal (and/or transverse or parallel) to the bone plate and/or to an outer surface region of the bone plate. In some examples, a beam axis for viewing the bone and bone plate assembly radiographically may be selected by placing a landmark of the handle in juxtaposition with (near or overlapping) a feature of the bone plate in one or more radiographic images. The marker of the targeting guide and/or the alignment region of the handle may form a line segment and/or define an axis in the radiographic images.

A position of the bone plate on the bone may be adjusted (e.g., while viewed fluoroscopically), during and/or after generation of one or more radiographic images. Adjustment of bone plate position may be based on the radiographic image(s). The position may be adjusted by pivoting the bone plate, moving the bone plate translationally, or both. In some embodiments, the position may be adjusted by sliding the bone on a surface region of a bone, such as on volar surface region of a distal part of a radial bone or on a distal tibial surface region. In some cases, the position of the bone plate may be adjusted if the line segment formed in one or more images by the guide marker does not point adequately at a landmark of the bone in the image and/or if an alignment region of the handle does not line up sufficiently with the shaft of the bone. Any suitable anatomical landmark of bone may be utilized in conjunction with the guide marker, generally a protrusion (a process) or a recess, such as a tuberosity, a fossa, a condyle, or the like. In some cases, the landmark may be the radial styloid and particularly a tip thereof.

The position of the bone plate may be stabilized by pressing a miniature cleat of the bone plate into bone, such that the cleat forms and occupies an indentation in the bone. After stabilization, the bone plate may be imaged additionally, such as with different views (e.g., a medial-lateral view of the bone and/or a transverse view of the bone plate, among others). If the position of the bone plate is acceptable, the position of the bone plate may be stabilized further by placement of one or more fasteners, such as a K-wire, through one or more apertures of the bone plate and into bone. If the position of the bone plate is not acceptable, the cleat may be removed from the indentation, which permits the bone plate to be re-positioned on bone, and then the cleat may be pressed into bone again at one or more other positions.

The bone plate may be secured to the bone by placement of a plurality of fasteners through apertures of the bone plate and into bone. Any suitable fasteners may be used for attaching or securing the bone plate to bone, such as bone screws, wires, or the like.

VII. Kits

The system disclosed herein may be provided as a kit. The kit may include at least one bone plate, a targeting guide, a handle, fasteners (e.g., bone screws and/or wires, among others) to attach the bone plate to bone and/or the targeting guide and/or handle to the bone plate, a drill, guide cannulas, a driver, and/or the like. Any of the components of a kit may be supplied in a sterile package. Some of the components may be configured to be re-used (e.g., the drill, guide cannulas, handle, targeting guide, and/or driver) and others may be configured to be used only once (e.g., the bone plate and fasteners).

VIII. EXAMPLES

The following examples describe additional aspects of exemplary bone fixation systems including a bone plate, a handle, and/or a targeting guide. These examples are intended for illustration and should not limit the entire scope of the present disclosure.

Example 1

Exemplary Radiographic Images

Figure 13:
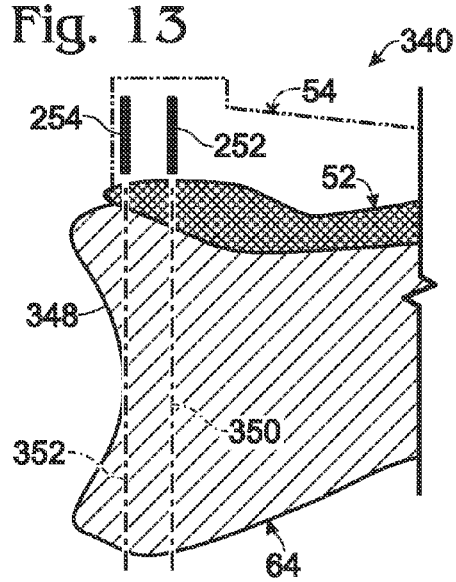
FIG. 13 is a somewhat schematic representation of an exemplary radiographic image of the bone fixation system and radial bone of FIG. 1, taken generally along line 13-13 of FIG. 12 by fluoroscopy using a radiation beam having a beam axis that is orthogonal to the axes defined by distal markers of the targeting guide but skewed from a plane defined by the distal markers, in accordance with aspects of present disclosure.
Figure 14:
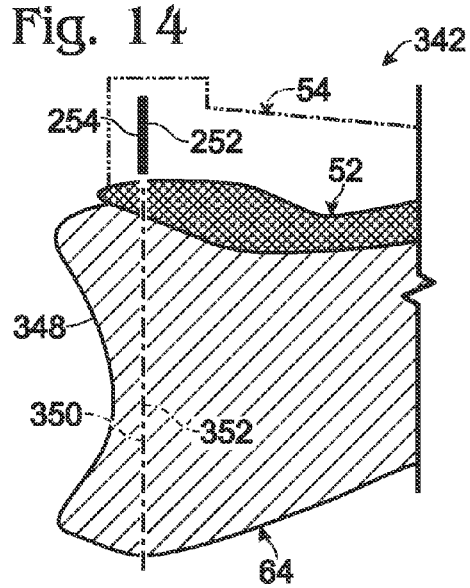
FIG. 14 is a somewhat schematic representation of another exemplary radiographic image of the bone fixation system and radial bone of FIG. 1, taken generally along line 14-14 of FIG. 12 by fluoroscopy using a radiation beam having a beam axis that is orthogonal to the axes defined by distal markers of the targeting guide and parallel to a plane defined by the distal markers, in accordance with aspects of present disclosure.

This example describes exemplary radiographic images that may be generated with an exemplary bone fixation system disposed on an exemplary bone; see FIGS. 12-14.

Relative radiopacity is indicated in the images by shading, with bone 64 being less radiopaque than bone plate 52, which in turn is less radiopaque than markers 252-256 and extension portion 142 of handle 56. Structures that block X-rays most efficiently are darkest in the images, and would be lightest in negative versions of the images.

FIG. 12 shows an exemplary radiographic image 320 of bone fixation system 50 and radial bone 64 (see FIG. 1). Fasteners 58, 60 are not shown to simplify the presentation. Image 320 may be generated using a radiation beam having a beam axis that is orthogonal to a plane defined by bone plate 52, and is directly along an anterior-posterior through the bone. A surgeon can find the proper beam axis for the image shown by adjusting the beam axis until there is a visible juxtaposition, indicated at 322, of landmark 220 and edge feature 222.

The surgeon then may refer to markers 252-256 and alignment region 186 to check and refine the position of the bone plate on the bone. Markers 252, 254 opposingly flank the most medial and lateral positions of prospective bone screws and thus may be consulted to adjust the side-to-side position of the head portion of the bone plate across the bone. Marker 256 predicts a prospective trajectory 324 of styloid screw 70 (also see FIG. 4). Marker 256 appears as a line segment in the image. The line segment points to the tip of radial styloid 122, indicating proper orientation of bone plate 52 in an anterior-posterior plane. If necessary or desired, the plate can be moved (e.g., pivoted) to change the prospective screw trajectory, such as by pointing marker 256 more toward the tip of the radial styloid. Alignment region 186 provides an indicator for centering body portion 80 across the bone. The plate can be moved (e.g., pivoted) to position alignment region 186 more coaxial to shaft portion 214 of the bone in the image.

FIGS. 13 and 14 show radiographic images 340, 342 taken as indicated in FIG. 12 with respective beam axes 344, 346 that are skewed from each other. (Marker 256 is not shown in images 340, 342.) In FIG. 13, beam axis 344 is orthogonal to the beam axis used to generate image 320 of FIG. 12, and thus is skewed from a plane defined collectively by markers 252, 254. (The plane is generally parallel to a radiocarpal articular surface 348 formed by radial bone 64, which is tilted radially and volarly with respect to orthogonal to the long axis of the bone.) Accordingly, markers 252, 254 are resolved into two line segments (bars) in image 340, which define axes 350, 352 that are parallel and spaced from each other. In image 340, neither axis is an accurate indication of the prospective distal boundary of bone screws placed into distal apertures of the bone plate. In FIG. 14, beam axis 346 is oriented parallel to the plane defined by markers 252, 254, and orthogonal to each of markers 252, 254 (because the markers are not longitudinally offset from each other in the image). As a result, axes 350, 352 are superposed and provide an accurate indication of the prospective distal boundary of bone screws placed into the distal apertures the bone plate. For example, in FIG. 14, axes 350, 352 are spaced from distal articular surface 348, which predicts that bone screws placed into the distal apertures of the bone plate will not enter the radiocarpal joint.

Example 2

Selected Embodiments I

This example describes selected embodiments of the present disclosure involving a handle, presented as a series of indexed paragraphs.

1. A method of situating a bone plate on bone, comprising: (A) connecting a targeting guide and a handle to a bone plate to form an assembly; (B) detecting one or more radiographic images of the assembly with the assembly disposed on a surface region of a bone; and (C) positioning the assembly on the surface region based on a pair of nonparallel axes defined in the images by the targeting guide and the handle.

2. The method of paragraph 1, wherein the step of positioning the assembly is based on first and second axes arranged obliquely to each other.

3. The method of paragraph 2, wherein the first axis is defined by a relatively radiopaque pin attached to and disposed in a relatively radiolucent body of the targeting guide 4. The method of paragraph 2, wherein the first axis is configured to extend near or intersect a landmark of the bone in the images when the bone plate is correctly positioned on the bone.

5. The method of paragraph 2, wherein the second axis is configured to be substantially aligned with a shaft of the bone in the images when the bone plate is correctly positioned on the bone.

6. The method of paragraph 2, wherein the handle includes an alignment section that defines the second axis and that is offset orthogonally and longitudinally from the bone plate.

7. The method of paragraph 1, wherein the step of detecting includes a step of detecting images taken orthogonally to the bone plate.

8. The method of paragraph 1, wherein the step of detecting includes a step of selecting a viewing direction orthogonal to the bone plate based on overlap or close approach, in one or more radiographic images, of a landmark of the handle with a feature of the bone plate.

9. The method of paragraph 8, wherein the landmark is a bend in the handle.

10. The method of paragraph 1, wherein the handle and the targeting guide are connected separately to the bone plate.

11. A method of situating a bone plate on bone, comprising: (A) connecting a targeting guide and a handle to a bone plate to form an assembly; (B) detecting one or more radiographic images of the assembly with the assembly disposed on a surface region of a bone; and (C) positioning the assembly on the surface region based on an axis defined in the images by the targeting guide, the handle, or both.

12. The method of paragraph 11, wherein the bone plate defines a set of orthogonal axes, wherein the targeting guide includes an elongate, relatively radiopaque member that defines an axis oriented obliquely to each of the orthogonal axes of the bone plate, and where the step of positioning is based on the axis defined by the radiopaque member.

13. The method of paragraph 11, wherein the targeting guide and the handle are discrete from one another and connected separately to the bone plate.

14. The method of paragraph 11, further comprising a step of selecting a direction of view orthogonal to the bone plate for the step of detecting based on a relative disposition of the handle and the bone plate in one or more radiographic images.

15. A method of bone fixation, comprising: (A) fastening a handle assembly to a bone plate defining a long axis, the handle assembly including an extension portion connected to a graspable grip portion, the extension portion providing a radiopaque alignment region that is offset from the bone plate along the long axis; (B) generating one or more radiographic images of the alignment region disposed above a shaft portion of a long bone while the bone plate is disposed on an end portion of the long bone that is wider than the shaft portion; (C) adjusting an orientation of the bone plate on the long bone based on a relative alignment of the alignment region and the shaft portion in the radiographic images; (D) securing the bone plate to the long bone; and (E) disconnecting the handle assembly from the bone plate.

16. The method of paragraph 15, wherein the bone plate defines a plane, and wherein the step of generating one or more radiographic images is performed using a beam of radiation having a beam axis that is substantially orthogonal to the plane of the bone plate.

17. The method of paragraph 15 or paragraph 16, wherein less than one-half of a length of the alignment region overlaps the bone plate along the long axis.

18. The method of any one of paragraphs 15 to 17, wherein the long bone is a radial bone, and wherein the end portion is a distal portion of the radial bone.

19. The method of any one of paragraphs 15 to 18, wherein the step of adjusting an orientation of the bone plate includes a step of positioning the alignment region substantially coaxial to the shaft portion of the long bone in at least one of the radiographic images.

20. The method of any one of paragraphs 15 to 19, wherein the alignment region is substantially narrower than the bone plate.

21. The method of any one of paragraphs 15 to 20, wherein the alignment region is cylindrical.

22. A method of bone fixation, comprising: (A) selecting a bone plate including a head portion connected to an elongated body portion, the body portion being narrower than the head portion and defining a plane and a long axis; (B) fastening a handle assembly to the bone plate, the handle assembly including an extension portion connected to a graspable grip portion, the extension portion providing a radiopaque alignment region that is offset from the bone plate along the long axis in a direction away from the head portion; (C) generating radiographic images of the alignment region disposed above a shaft portion of a long bone while the bone plate is disposed on an end portion of the long bone and using a beam of radiation having a beam axis oriented substantially orthogonal to the plane of the bone plate; (D) positioning the alignment region to be substantially parallel to the shaft portion of the long bone in one or more of the radiographic images; (E) securing the bone plate to the long bone; and (F) disconnecting the handle assembly from the bone plate.

23. The method of paragraph 22, further comprising a step of forming a radiographically visible juxtaposition of a landmark of the extension portion with an edge feature of the bone plate in one or more radiographic images, wherein the juxtaposition signifies that the beam axis is substantially orthogonal to the plane.

24. The method of paragraph 23, wherein the landmark of the extension portion is created by a bend in the extension portion, a change in width of the extension portion, an aperture of the extension portion, or a combination thereof.

25. The method of paragraph 23 or paragraph 24, wherein the bone plate has an outer edge that forms a perimeter of the bone plate and has a plurality of inner edges that bound apertures of the bone plate, and wherein the edge feature is created by the outer edge at an end of the bone plate.

26. The method of any one of paragraphs 22 to 25, wherein the bone plate has an end formed by the body portion, wherein the handle assembly is fastened at a site of the bone plate that is spaced from the end such that one or more apertures of the bone plate are disposed between the site and the end, and wherein the extension portion extends along a path having a transverse offset such that the extension member does not obstruct placement of fasteners into the one or more apertures.

27. The method of any one of paragraphs 22 to 26, wherein the step of fastening includes a step of installing at least one fastener that engages the handle assembly and the bone plate.

28. The method of any one of paragraphs 22 to 27, wherein the step of positioning includes a step of positioning the alignment region to be substantially coaxial to the shaft portion of the long bone in one or more of the radiographic images.

29. A method of bone fixation, comprising: (A) selecting a bone plate including a head portion connected to an elongated body portion, the body portion being narrower than the head portion and defining a long axis; (B) selecting a handle assembly including a base portion, a graspable grip portion, and an extension portion connecting the grip portion to the base portion, the extension portion providing a radiopaque alignment region; (C) fastening the bone plate to the handle assembly at the base portion with at least one threaded fastener; (D) disposing the bone plate on an end portion of a long bone and the alignment region above a shaft portion of the long bone, with the alignment region and the shaft portion defining respective long axes that are substantially coplanar to each other; (E) securing the bone plate to the long bone; and (F) disconnecting the handle assembly from the bone plate.

30. The method of paragraph 29, wherein less than one-half of a length of the alignment region overlaps the body portion of the bone plate along the long axis defined by the body portion.

31. The method of paragraph 29 or paragraph 30, wherein the long bone is a radial bone, and wherein the end portion of the long bone is a distal portion of the radial bone.

32. The method of any one of paragraphs 29 to 31, wherein the alignment region defines a long axis that is parallel to the long axis defined by the body portion of the bone plate.

33. The method of any one of paragraphs 29 to 32, wherein the bone plate has an end formed by the body portion, wherein the handle assembly is fastened at a site of the bone plate that is spaced from the end such that one or more apertures of the bone plate are disposed between the site and the end, and wherein the handle assembly along a path having a transverse offset such that the handle assembly does not obstruct placement of fasteners into the one or more apertures.

34. The method of any one of paragraphs 29 to 33, wherein the alignment region is substantially narrower than the bone plate and cylindrical.

35. A system for bone fixation, comprising: (A) a bone plate including a head portion connected to an elongated body portion, the body portion being narrower than the head portion and defining a plane and a long axis; and (B) a handle assembly configured to be fastened to the bone plate and including an extension portion connected to a graspable grip portion, the extension portion providing a radiopaque alignment region, wherein, when the bone plate is fastened to the handle assembly and disposed on an end portion of a long bone, the alignment region is offset from the body portion of the bone plate along the long axis in a direction away from the head portion and is configured to be disposed above a shaft portion of the long bone and aligned with the shaft portion of the long bone in one or more radiographic images generated with a beam of radiation having a beam axis transverse to the plane.

36. The system of paragraph 35, wherein the alignment region is configured to be aligned with the shaft portion of the long bone in radiographic images generated with a beam of radiation having a beam axis substantially orthogonal to the plane.

37. The system of paragraph 35 or paragraph 36, wherein the alignment region is configured to be aligned coaxially with the shaft portion of the long bone in the radiographic images.

38. The system of any preceding paragraph, wherein the bone plate has an inner surface region contoured to fit onto an end portion of a long bone.

39. The system of paragraph 38, wherein the inner surface region of the bone plate is contoured to fit onto a distal end portion of a radial bone.

40. The system of any preceding paragraph, wherein the alignment region defines an alignment axis that is substantially parallel to the long axis defined by the body portion of the bone plate.

41. The system of any preceding paragraph, wherein the alignment region is cylindrical.

42. The system of any preceding paragraph, further comprising a threaded fastener configured to fasten the handle assembly to the bone plate.

43. The system of paragraph 42, wherein the threaded fastener is a thumbscrew.

44. The system of any preceding paragraph, wherein a landmark of the extension portion is juxtaposed with an edge feature of the bone plate in radiographic images collected when the beam axis is substantially orthogonal to the plane.

45. The system of paragraph 44, wherein the landmark of the extension portion is created by a bend in the extension portion, a change in width of the extension portion, an aperture of the extension portion, or a combination thereof.

46. The system of paragraph 44 or paragraph 45, wherein the bone plate has an outer edge that forms a perimeter of the bone plate and has a plurality of inner edges that bound apertures of the bone plate, and wherein the edge feature is created by the outer edge at an end of the body portion of the bone plate.

47. The system of any preceding paragraph, wherein less than one-half a length of the alignment region overlaps the bone plate along the long axis when the handle assembly is fastened to the bone plate.

48. The system of paragraph 47, wherein substantially none of the alignment region overlaps the bone plate along the long axis when the handle assembly is fastened to the bone plate.

49. The system of any preceding paragraph, wherein the alignment region is substantially narrower than the body portion of the bone plate.

50. The system of any preceding paragraph, wherein the bone plate has an end formed by the body portion, wherein the handle assembly is configured to be fastened at a site of the bone plate that is spaced from the end such that one or more apertures of the bone plate are disposed between the site and the end, and wherein the extension portion extends along a path having a transverse offset such that the extension member does not obstruct placement of fasteners into the one or more apertures.

Example 3

Selected Embodiments II

This example describes selected embodiments of the present disclosure involving a targeting guide in the form of a guide block, presented as a series of indexed paragraphs.

1. A method of bone fixation, comprising: (A) selecting a bone plate including an outer surface region and defining a plurality of apertures; (B) selecting a guide block defining a plurality of openings and including a radiolucent body and at least one elongated, radiopaque marker disposed in and affixed to the radiolucent body; (C) attaching the guide block to the bone plate with the guide block over the outer surface region of the bone plate and such that openings of the guide block are adjacent to and in coaxial alignment with apertures of the bone plate, wherein attached is performed after the at least one marker is affixed to the radiolucent body; (D) disposing the bone plate on bone; (E) securing the bone plate to the bone with fasteners placed in one or more of the apertures of the bone plate; and (F) disconnecting the guide block from the bone plate.

2. The method of paragraph 1, further comprising a step of forming one or more holes in the bone that are coaxial with one or more of the apertures of the bone plate, wherein the step of forming is performed with the guide block attached to the bone plate.

3. The method of paragraph 2, wherein the step of forming one or more holes is performed by installing one or more self-drilling fasteners into the bone.

4. The method of any one of paragraphs 1 to 3, wherein the step of securing the bone plate to bone is performed while the guide block is attached to the bone plate.

5. The method of any one of paragraphs 1 to 4, wherein the step of attaching the guide block to the bone plate is performed before or after the bone plate is disposed on the bone.

6. The method of any one of paragraphs 1 to 5, wherein the step of attaching the guide block to the bone plate includes a step of attaching the guide block to the bone plate with a threaded fastener.

7. The method of paragraph 6, wherein the threaded fastener is a thumbscrew.

8. The method of any one of paragraphs 1 to 7, further comprising a step of generating at least one radiographic image of the bone with the bone plate disposed on the bone and attached to the guide block, wherein the radiographic image is generated with a beam of radiation having a beam axis oriented at least generally orthogonal to a plane defined by the bone plate, and wherein the marker forms a line segment in the radiographic image.

9. The method of paragraph 8, wherein the line segment overlaps the bone plate in the radiographic image.

10. The method of paragraph 9, wherein at least one-half of a length of the line segment is disposed inside a perimeter of the bone plate in the radiographic image.

11. The method of any one of paragraphs 8 to 10, wherein the line segment points to a process of the bone in the radiographic image.

12. The method of paragraph 11, wherein the line segment points to a styloid process on a radial bone in the radiographic image.

13. The method of any one of paragraphs 1 to 12, further comprising a step of moving the bone plate with respect to the bone based on a position of the line segment marker relative to the bone in the one or more radiographic image.

14. The method of any one of paragraphs 1 to 13, wherein the marker is affixed substantially permanently to the radiolucent body.

15. A method of bone fixation, comprising: (A) disposing a bone plate on a bone, the bone plate including an outer surface and defining a plurality of apertures that extend through the bone plate from the outer surface; (B) attaching a guide block to the bone plate with the guide block over the outer surface such that openings of the guide block are in coaxial alignment with the apertures of the bone plate, the guide block including at least one elongated, radiopaque marker disposed in and affixed to the radiolucent body; (C) generating at least one radiographic image of the bone with the bone plate disposed on the bone and the guide block attached to the bone plate; (D) adjusting a position of the bone plate on the bone based at least in part on a position of the marker with respect to the bone in the radiographic image; and (E) securing the bone plate to the bone.

16. A method of bone fixation, comprising: (A) selecting a bone plate defining a plurality of apertures and a guide block including a radiolucent body defining a plurality of openings and also including at least one elongated, radiopaque marker disposed in and affixed to the radiolucent body, the guide block being attached or attachable to the bone plate such that openings of the guide block are adjacent to and in coaxial alignment with apertures of the bone plate; (B) generating one or more radiographic images of the bone with the bone plate disposed on the bone and attached to the guide block, wherein, in at least one of the radiographic images, the marker defines an axis parallel to a prospective trajectory of a fastener extending coaxially to an aperture of the bone plate into the bone; (C) securing the bone plate to the bone; and (D) disconnecting the guide block from the bone plate.

17. The method of paragraph 16, wherein the marker defines an axis that is substantially coaxial to the prospective trajectory in the at least one radiographic image.

18. The method of paragraph 16 or paragraph 17, wherein the bone is a radial bone, and wherein the axis intersects the radial styloid of the radial bone in the at least one radiographic image.

19. The method of paragraph 16, further comprising a step of adjusting a position of the bone plate on the bone based on a position of the axis with respect to the bone in the at least one radiographic image.

20. The method of paragraph 19, wherein the step of adjusting includes a step of adjusting a position of the bone plate such that the marker points to a tip of a process formed by the bone in at least one other of the radiographic images.

21. The method of any one of paragraphs 16 to 20, wherein the bone plate defines a plane, wherein the at least one radiographic image is generated using a beam of radiation having a beam axis oriented at least generally orthogonal to the plane, and wherein at least a majority of the marker is disposed inside a perimeter of the bone plate in the at least one radiographic image.

22. The method of any one of paragraphs 16 to 21, wherein the marker is distinguishable from the bone plate and the bone plate is distinguishable from the bone in the at least one radiographic image, and wherein the radiographic images are generated with the at least one marker disposed completely outside the bone.

23. The method of any one of paragraphs 16 to 22, wherein the at least one marker includes a pair of elongate, radiopaque markers that are parallel to each other, and wherein the pair of markers overlap each other in the at least one radiographic image.

24. The method of paragraph 23, wherein the step of generating is performed using a beam of radiation having a beam axis, further comprising a step of moving the beam axis, the bone, or both, to increase an amount of overlap of the pair of markers in radiographic images.

25. The method of paragraph 23 or paragraph 24, wherein the pair of markers collectively define a plane that is parallel to prospective trajectories of two or more fasteners from a row of two more apertures of the bone plate into the bone.

26. The method of any one of paragraphs 16 to 25, wherein an opening of the guide block is aligned coaxially with the aperture of the bone plate, further comprising a step of forming a hole in the bone that is coaxial with the opening and the aperture.

27. A method of bone fixation, comprising: (A) disposing a bone plate on a bone, the bone plate including an outer surface region and defining a plurality of apertures; (B) generating at least one radiographic image of the bone, with the bone plate disposed on the bone and attached to a guide block, with the guide block over the outer surface region such that openings of the guide block are adjacent to and in coaxial alignment with the apertures of the bone plate, the guide block including a radiolucent body that defines the openings and at least one elongated, radiopaque marker disposed in and affixed substantially permanently to the radiolucent body; (C) adjusting a position of the bone plate on the bone based on a position of the at least one marker with respect to the bone in the radiographic image; and (D) securing the bone plate to the bone.

28. The method of paragraph 27, wherein the at least one marker includes a pair of elongated, radiopaque markers that are not parallel to each other.

29. The method of paragraph 27 or paragraph 28, wherein the at least one marker includes a pair of elongated, radiopaque markers that are parallel to each other and spaced from each other in a direction transverse to axes defined by the markers.

30. The method of paragraph 29, wherein the at least one marker includes the pair of markers that are parallel to each other and another elongate, radiopaque marker that is oblique to the pair of markers.

31. The method of any one of paragraphs 27 to 30, wherein the bone plate is formed of metal and the radiolucent body of the guide block is formed of plastic.

32. The method of any one of paragraphs 27 to 31, wherein the bone is a radial bone, wherein the bone plate defines a row of two or more distal apertures, wherein the at least one marker includes first and second elongate, radiopaque markers that collectively define a plane parallel and adjacent to axes defined by the distal apertures.

33. The method of any one of paragraphs 27 to 32, wherein the step of generating is performed with the at least one marker disposed completely outside the bone.

34. A method of bone fixation, comprising: (A) selecting a bone plate including an outer surface region and defining a plurality of apertures; (B) selecting a guide block including a radiolucent body defining a plurality of openings and also including at least one elongated, radiopaque marker affixed to the radiolucent body; (C) attaching the guide block to the bone plate with the guide block contacting the outer surface region of the bone plate and such that openings of the guide block are adjacent to and in coaxial alignment with apertures of the bone plate; (D) disposing the bone plate on bone; (E) adjusting a position of the bone plate on the bone based on a position of the marker with respect to the bone in one or more radiographic images; and (F) securing the bone plate to the bone.

35. The method of paragraph 34, wherein the bone is a radial bone, wherein the bone plate defines a row of two or more distal apertures, wherein the at least one marker includes first and second elongate, radiopaque markers that collectively define a plane parallel and adjacent to axes defined by the distal apertures.

36. A bone fixation system, comprising: (A) a bone plate including an outer surface region and defining a plurality of apertures for receiving fasteners that secure the bone plate to bone; and (B) a guide block attached or attachable to the bone plate with the guide block directly above the outer surface region of the bone plate such that openings of the guide block are adjacent to and in coaxial alignment with apertures of the bone plate, the guide block including a radiolucent body that defines the openings and also including at least one elongated, radiopaque marker affixed to the radiolucent body.

37. The bone fixation system of paragraph 36, wherein the at least one marker is affixed substantially permanently to the radiolucent body.

38. The bone fixation system of paragraph 36 or paragraph 37, wherein the radiolucent body is a single piece.

39. The bone fixation system of any one of paragraphs 36 to 38, wherein the bone plate includes a wider head portion connected to a narrower, elongated body portion, and wherein the guide block selectively overlaps the head portion relative to the body portion.

40. The bone fixation system of any one of paragraphs 36 to 39, wherein the at least one marker includes a marker defining an axis that is adjacent to an opening of the guide block and substantially parallel to and/or substantially coplanar with another axis defined collectively by the opening and an aperture of the bone plate aligned coaxially with the opening when the guide block is attached to the bone plate.

41. The bone fixation system of any one of paragraphs 36 to 40, wherein the at least one marker includes a pair of markers defining spaced axes that are substantially parallel to each other.

42. The bone fixation system of any one of paragraphs 36 to 41, wherein the bone plate defines a plane, and wherein at least a majority of the marker is disposed inside a perimeter of the bone plate in a radiographic image of the bone, bone plate, and attached guide block generated using a beam of radiation having a beam axis oriented orthogonal to the plane.

43. The bone fixation system of any one of paragraphs to 36 to 42, wherein the bone plate has an inner surface region contoured to fit onto a surface region of a bone, wherein the at least one marker includes a marker configured to point to a feature of the bone in a radiographic image of the bone taken with the bone plate fitted onto the surface region of a bone, the guide block attached to the bone plate, and using a beam of radiation having a beam axis oriented transverse to the inner surface region.

44. The bone fixation system of paragraph 43, wherein the feature is a tip of a process formed by the bone.

45. The bone fixation system of any one of paragraphs 36 to 44, wherein the bone plate has an inner surface, and wherein the at least one marker does not project substantially from the inner surface when the guide block is attached to the bone plate.

46. A bone fixation system, comprising: (A) a bone plate including a head portion and an elongated body portion, the head portion having an outer surface and defining a plurality of apertures for receiving fasteners that secure the bone plate to bone; and (B) a guide block attached or attachable to the bone plate with the guide block directly above the outer surface region of the head portion such that openings of the guide block are adjacent to and in coaxial alignment with apertures of the head portion, the guide block including a one-piece, radiolucent body that defines the openings and also including at least one elongated, radiopaque marker affixed substantially permanently to the radiolucent body.

47. The bone fixation system of paragraph 46, wherein the bone plate has an inner surface region contoured to fit onto a distal surface region of a radial bone.

48. The bone fixation system of paragraph 46 or paragraph 47, wherein the at least one marker includes a pair of markers defining spaced axes that are substantially parallel to each other, wherein the spaced axes are parallel to and spaced from a plurality of axes defined by openings of the guide block that are configured to be aligned coaxially with a row of two or more apertures of the bone plate, and wherein the spaced axes collectively define a plane representing a boundary for bone screws placed in the row of apertures.

49. The bone fixation system of any one of paragraphs 46 to 48, wherein the bone plate has an inner surface region contoured to fit onto a surface region of a bone, wherein the at least one marker includes a marker configured to point to a tip of a radial styloid in a radiographic image of the bone taken with the bone plate at least generally fitted onto the surface region of a bone, the guide block attached to the bone plate, and using a beam of radiation having a beam axis oriented transverse to the inner surface region.

50. The bone fixation system of paragraph 49, wherein the bone plate defines a plane, and wherein the beam axis is orthogonal to the plane.

51. A method of bone fixation, comprising: (A) disposing a bone plate on a bone, the bone plate including an outer surface region and defining a plurality of apertures; (B) generating at least one radiographic image of the bone, with the bone plate disposed on the bone and attached to a guide block, with the guide block over the outer surface region such that openings of the guide block are adjacent to and in coaxial alignment with the apertures of the bone plate, the guide block including a radiolucent body that defines the openings and at least one elongated, radiopaque marker disposed in and affixed to the radiolucent body; (C) adjusting a position of the bone plate on the bone based on a position of the at least one marker with respect to the bone in the radiographic image; and (D) securing the bone plate to the bone.

52. The method of paragraph 51, wherein, in the at least one radiographic image, the marker defines an axis parallel to a prospective trajectory of a fastener extending coaxially to an aperture of the bone plate into the bone.

53. The method of paragraph 51 or paragraph 52, wherein the marker defines an axis that is substantially coaxial to the prospective trajectory in the at least one radiographic image.

54. The method of any one of paragraphs 51 to 53, wherein the bone plate defines a plane, wherein the at least one radiographic image is generated using a beam of radiation having a beam axis oriented at least generally orthogonal to the plane, and wherein at least a majority of the marker is disposed inside a perimeter of the bone plate in the at least one radiographic image.

55. The method of any one of paragraphs 51 to 54, wherein the at least one radiographic image is generated with the at least one marker disposed completely outside the bone.

56. A bone fixation system, comprising: (A) a bone plate including an outer surface region and defining a plurality of apertures for receiving fasteners that secure the bone plate to bone; and (B) a guide block attached or attachable to the bone plate over the outer surface region of the bone plate such that openings of the guide block are adjacent to and in coaxial alignment with apertures of the bone plate, the guide block including a radiolucent body that defines the openings and also including at least one elongated, radiopaque marker affixed to the radiolucent body.

57. The bone fixation system of paragraph 56, wherein the at least one marker is affixed substantially permanently to the radiolucent body.

58. The bone fixation system of paragraph 56 or paragraph 57, wherein the at least one marker includes a first marker defining an axis that is adjacent to an opening of the guide block and substantially parallel to and/or substantially coplanar with another axis defined collectively by the opening and an aperture of the bone plate configured to be aligned coaxially with the opening.

59. The bone fixation system of any one of paragraphs 56 to 58, wherein the at least one marker includes a pair of markers defining spaced axes that are substantially parallel to each other.

60. The bone fixation system of paragraph 59, wherein the spaced axes are parallel to and spaced from a plurality of axes defined by openings of the guide block that are configured to be aligned coaxially with a row of two or more apertures of the bone plate.

61. The bone fixation system of paragraph 60, wherein the spaced axes collectively define a plane representing a boundary for bone screws placed in the row of apertures.

62. The bone fixation system of paragraph 61, wherein the outer surface region defines a plane, and wherein the spaced axes are transverse to the plane.

63. The bone fixation system of any one of paragraphs 56 to 62, wherein the bone plate has an inner surface region contoured to fit onto a surface region of a bone, wherein the at least one marker includes a marker configured to point to a feature of the bone in a radiographic image of the bone taken with the bone plate fitted onto the surface region, the guide block attached to the bone plate, and using a beam of radiation having a beam axis oriented transverse to the inner surface region.

64. The bone fixation system of paragraph 63, wherein the bone plate defines a plane, and wherein the beam axis is orthogonal to the plane.

65. The bone fixation system of any one of paragraphs 56 to 64, wherein the bone plate includes a wider head portion connected to a narrower, elongated body portion, and wherein the guide block selectively overlaps the head portion relative to the body portion.

66. The bone fixation system of any one of paragraphs 56 to 65, wherein the radiolucent body is formed of plastic and the at least one marker is formed of metal.

67. The bone fixation system of any one of paragraphs 56 to 66, wherein the bone plate is formed of metal.

68. The bone fixation system of any one of paragraphs 56 to 67, wherein the guide block is substantially thicker than the bone plate.

69. The bone fixation system of any one of paragraphs 56 to 68, wherein the bone plate includes a wider head portion connected to a narrower, elongated body portion, and wherein the guide block selectively overlaps the head portion.

70. The bone fixation system of any one of paragraphs 56 to 69, further comprising a thumbscrew configured to attach the guide block to the bone plate.

71. The bone fixation system of any one of paragraphs 56 to 70, wherein the bone plate defines a plane, and wherein at least a majority of the marker is disposed inside a perimeter of the bone plate in a radiographic image of the bone, bone plate, and attached guide block generated using a beam of radiation having a beam axis oriented orthogonal to the plane.

72. The bone fixation system of any one of paragraphs 56 to 71, wherein the marker does not project substantially from an inner surface of the radiolucent body.

73. The bone fixation system of any one of paragraphs 56 to 72, wherein the marker also does not project substantially from an outer surface of radiolucent body.

74. The bone fixation system of any one of paragraphs 56 to 73, wherein the bone plate and the marker are each formed of metal.

75. The bone fixation system of any one of paragraphs 56 to 74, wherein the bone plate is formed substantially of titanium, and wherein the at least one marker is formed of stainless steel.

76. The bone fixation system of any one of paragraphs 56 to 75, wherein the bone plate has an inner surface region contoured to fit onto a distal surface region of a radial bone.

77. The bone fixation system of any one of paragraphs 56 to 76, wherein the bone plate has an inner surface, and wherein the at least one marker does not project substantially from the inner surface when the guide block is attached to the bone plate.

78. The bone fixation system of any one of paragraphs 56 to 77, wherein the radiolucent body is a single piece.

79. The bone fixation system of any one of paragraphs 56 to 78, further comprising a guide tube configured to be received interchangeably in individual openings of the guide block.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

We claim:

1. A bone fixation system, comprising:
   a bone plate including an outer surface region and defining a long axis and a plane extending along the long axis and parallel to the outer surface region of the bone plate, the bone plate also defining a plurality of apertures for receiving fasteners that secure the bone plate to bone; and
   a guide block attached or attachable to the bone plate with the guide block above the outer surface region of the bone plate such that openings of the guide block are adjacent to and in coaxial alignment with apertures of the bone plate, the guide block including a radiolucent body that defines the openings and also including at least one radiopaque marker affixed to the radiolucent body and elongated transverse to the plane.

2. The bone fixation system of claim 1, wherein the bone plate includes a wider head portion connected to a narrower, elongated body portion, and wherein the guide block selectively overlaps the head portion relative to the body portion.

3. The bone fixation system of claim 1, wherein the at least one marker includes a pair of markers defining spaced axes that are substantially parallel to each other.

4. The bone fixation system of claim 1, wherein at least a majority of the marker is disposed inside a perimeter of the bone plate in a radiographic image of the bone, bone plate, and attached guide block generated using a beam of radiation having a beam axis oriented orthogonal to the plane.

5. The bone fixation system of claim 1, wherein the bone plate has an inner surface region contoured to fit onto a surface region of a bone, wherein the at least one marker includes a marker configured to point to a feature of the bone in a radiographic image of the bone taken with the bone plate fitted onto the surface region of a bone, the guide block attached to the bone plate, and using a beam of radiation having a beam axis oriented transverse to the inner surface region, and wherein the feature is a tip of a process formed by the bone.

6. A method of bone fixation, comprising:
   disposing a bone plate on a bone, the bone plate including an outer surface region and defining a plurality of apertures;
   generating at least one radiographic image of the bone, with the bone plate disposed on the bone and attached to a guide block, with the guide block over the outer surface region such that openings of the guide block are adjacent to and in coaxial alignment with the apertures of the bone plate, the guide block including a radiolucent body that defines the openings and at least one elongated, radiopaque marker disposed in and affixed to the radiolucent body;
   adjusting a position of the bone plate on the bone based on a position of the at least one marker with respect to the bone in the radiographic image; and
   securing the bone plate to the bone,
   wherein the bone plate defines a plane, wherein the at least one radiographic image is generated using a beam of radiation having a beam axis oriented at least generally orthogonal to the plane, and wherein at least a majority of the marker is disposed inside a perimeter of the bone plate in the at least one radiographic image.

7. The method of claim 6, wherein, in the at least one radiographic image, the marker defines an axis parallel to a prospective trajectory of a fastener extending coaxially to an aperture of the bone plate into the bone.

8. The method of claim 7, wherein the marker defines an axis that is substantially coaxial to the prospective trajectory in the at least one radiographic image.

9. The method of claim 6, wherein the at least one radiographic image is generated with the at least one marker disposed completely outside the bone.

10. A bone fixation system, comprising:
    a bone plate including an outer surface region and defining a plurality of apertures for receiving fasteners that secure the bone plate to bone; and
    a guide block attached or attachable to the bone plate with the guide block above the outer surface region of the bone plate such that openings of the guide block are adjacent to and in coaxial alignment with apertures of the bone plate, the guide block including a radiolucent body that defines the openings and also including at least one radiopaque marker affixed to the radiolucent body and elongated parallel to a through-axis defined by one of the openings.

11. The bone fixation system of claim 10, wherein the at least one marker is affixed substantially permanently to the radiolucent body.

12. The bone fixation system of claim 10, wherein the radiolucent body is a single piece.

13. The bone fixation system of claim 10, wherein the at least one marker includes a pair of markers defining spaced axes that are substantially parallel to each other, wherein the spaced axes are parallel to and spaced from a plurality of axes defined by openings of the guide block that are configured to be aligned coaxially with a row of two or more apertures of the bone plate, and wherein the spaced axes collectively define a plane representing a boundary for bone screws placed in the row of apertures.

14. The bone fixation system of claim 10, wherein the bone plate has an inner surface region contoured to fit onto a surface region of a bone, wherein the at least one marker includes a marker configured to point to a tip of a radial styloid in a radiographic image of the bone taken with the bone plate at least generally fitted onto the surface region of a bone, the guide block attached to the bone plate, and using a beam of radiation having a beam axis oriented transverse to the inner surface region.

15. A bone fixation system, comprising:
   a bone plate including an outer surface region and defining a plurality of apertures for receiving fasteners that secure the bone plate to bone; and
   a guide block having an upper surface region opposite a lower surface region and a plurality of openings extending from the upper surface region to the lower surface region, the guide block being attached or attachable to the bone plate with the lower surface region of the guide block adjacent the outer surface region of the bone plate and such that the openings of the guide block are in coaxial alignment with apertures of the bone plate, the guide block including a radiolucent body that defines the openings and also including at least one elongated, radiopaque marker affixed to the radiolucent body, the marker having an upper end that is closer to the upper surface region and opposite a lower end that is closer to the lower surface region.

16. The bone fixation system of claim 15, wherein the bone plate includes a wider head portion connected to a narrower, elongated body portion, and wherein the guide block selectively overlaps the head portion relative to the body portion.

17. The bone fixation system of claim 15, wherein the at least one marker includes a pair of markers defining spaced axes that are substantially parallel to each other.

18. The bone fixation system of claim 15, wherein the bone plate defines a plane, and wherein at least a majority of the marker is disposed inside a perimeter of the bone plate in a radiographic image of the bone, the bone plate, and the attached guide block generated using a beam of radiation having a beam axis oriented orthogonal to the plane.

19. The bone fixation system of claim 15, wherein the bone plate has an inner surface region contoured to fit onto a surface region of a bone, and wherein the at least one marker includes a marker configured to point to a feature of the bone in a radiographic image of the bone taken with the bone plate fitted onto the surface region of a bone, the guide block attached to the bone plate, and using a beam fof radiation having a beam axis oriented transverse to the inner surface region.

\* \* \* \* \*